(12) United States Patent
Pasternack et al.

(10) Patent No.: US 8,685,697 B1
(45) Date of Patent: Apr. 1, 2014

(54) LISTERIA MONOCYTOGENES BACTERIOPHAGES AND USES THEREOF

(71) Applicant: Intralytix, Inc., Baltimore, MD (US)

(72) Inventors: Gary Pasternack, Baltimore, MD (US); Alexander Sulakelidze, Townson, MD (US)

(73) Assignee: Intralytix, Inc., Baltimore, MD (US)

( * ) Notice: Subject to any disclaimer, the term of this patent is extended or adjusted under 35 U.S.C. 154(b) by 0 days.

(21) Appl. No.: 13/662,151

(22) Filed: Oct. 26, 2012

(51) Int. Cl.
*C12N 1/00* (2006.01)

(52) U.S. Cl.
USPC .......................................................... 435/243

(58) Field of Classification Search
USPC .......................................................... 435/243
See application file for complete search history.

(56) References Cited

U.S. PATENT DOCUMENTS

| | | |
|---|---|---|
| 8,148,131 B2 | 4/2012 | Kang et al. |
| 8,288,146 B2 | 10/2012 | Kang et al. |
| 8,293,515 B2 | 10/2012 | Shin et al. |

*Primary Examiner* — Karen Cochrane Carlson
*Assistant Examiner* — Jennifer M Tichy
(74) *Attorney, Agent, or Firm* — Hunton & Williams LLP

(57) ABSTRACT

The present invention is directed to isolated bacteriophages having specificity and lytic activity against strains of *Listeria* species, methods of using the bacteriophages, progeny and derivatives derived therefrom, to control the growth of *Listeria* species in various settings (e.g., food safety, sanitation, probiotics).

10 Claims, 1 Drawing Sheet

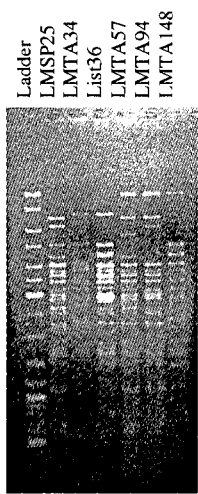
Gel: 0.8% Agarose gel
Condition: 23V
Duration: 17 hours
Digestion enzyme: SpeI
DNA ladder mix ( Fermentas, Inc.; Cat #SM0331)

LISTERIA MONOCYTOGENES BACTERIOPHAGES AND USES THEREOF

FIELD OF THE INVENTION

The present invention relates to seven novel bacteriophages designated LMSP-25, LMTA-34, LMTA-57, LMTA-94, and LMTA-148 (the "Deposited Bacteriophages"), and compositions comprising the same. More specifically, isolated bacteriophage compositions possessing lytic activity against strains of *Listeria* species including but not limited to *Listeria monocytogenes* (including serotypes: 1/2a, 1/2b, and 4b) (the "Targeted Bacteria") are provided in order to control the growth of the Targeted Bacteria, which may reduce their ability to contaminate and colonize various environments, including but not limited to (i) raw, unprocessed food products, (ii) equipment used to process or manufacture various food products, (iii) various food products processed or manufactured with equipment contaminated with the Targeted Bacteria, (iv) animals contaminated with the Targeted Bacteria, (v) animal environments contaminated with the Targeted Bacteria, and (vi) various processed food products for humans or animals containing ingredients contaminated with the Targeted Bacteria. The invention also provides methods for detecting the presence of the Targeted Bacteria in processed or unprocessed food products, and in equipment used to process or manufacture the food products. In addition, the invention provides methods of using the Deposited Bacteriophages to remove the Targeted Bacteria from medical, veterinary, animal husbandry, and other environments where they may be passed to animals including humans. Also, the invention provides methods of using the bacteriophage to prevent and treat animal and human diseases caused by the Targeted Bacteria as well as a probiotic.

BACKGROUND OF THE INVENTION

Bacteriophages

Bacteriophages are bacterial viruses that attach to their specific hosts and kill them by internal replication and bacterial lysis involving a complex lytic cycle involving several structural and regulatory genes. Phages are very specific in that they only attack their targeted bacterial hosts. They cannot infect human or other eukaryotic cells. Bacteriophages were first identified, in the early part of the 20th century by Frederick Twort and Felix D'Herelle who called them bacteriophages or bacteria-eaters (from the Greek phago meaning to eat or devour). Duckworth (1976) *Bacteriol Rev* 40(4): 793-802; Summers (1999) *Bacteriophage discovered. Felix d'Herelle and the origins of molecular biology*. New Haven, Conn., Yale University Press: 47-59.

Lytic and Lysogenic Bacteriophages

Bacteriophages have a lytic cycle or a lysogenic cycle, but few bacteriophages are capable of carrying out both. With lytic phages such as the T4 phage, bacterial cells are broken open (lysed) and destroyed after immediate replication of the virion. As soon as the cell is destroyed, the new bacteriophage viruses can find new hosts. Kutter and Sulakvelidze (2005) *Bacteriophages: Biology and Application*. CRC Press: 381-436.

In contrast, the lysogenic cycle does not result in immediate lysing of the host cell. Those phages able to undergo lysogeny are known as temperate phages. Their viral genome will integrate with host DNA and replicate along with it fairly harmlessly, or may even become established as a plasmid. The virus remains dormant until host conditions deteriorate (e.g., due to depletion of nutrients) then the endogenous phages (known as prophages) become active. At this point they initiate the reproductive cycle resulting in lysis of the host cell. As the lysogenic cycle allows the host cell to continue to survive and reproduce, the virus is reproduced in all of the host cell's offspring. See Kutter and Sulakvelidze (2005) *Bacteriophages: Biology and Application*.

Bacteriophage Structure

Although different bacteriophages may contain different materials they all contain nucleic acid and protein. Depending upon the phage, the nucleic acid can be either DNA or RNA but not both, and it can exist in various forms. The nucleic acids of phages often contain unusual or modified bases. These modified bases protect phage nucleic acid from nucleases that break down host nucleic acids during phage infection. The size of the nucleic acid varies depending upon the phage. The simplest phages only have enough nucleic acid to code for 3-5 average size gene products while the more complex phages may code for over 100 gene products. The number of different kinds of protein and the amount of each kind of protein in the phage particle will vary depending upon the phage. The simplest phage have many copies of only one or two different proteins while more complex phages may have many different kinds. The proteins function in infection and to protect the nucleic acid from nucleases in the environment. See also McGrath and van Sinderen (2007) Bacteriophage: Genetics and Molecular Biology.

Bacteriophage come in many different sizes and shapes. The basic structural features of bacteriophages include their size, head or capsid, tail. For example, T4, a common phage is among the largest phages; it is approximately 200 nm long and 80-100 nm wide. Other phages are smaller. Most phages range in size from 24-200 nm in length. All phages contain a head structure which can vary in size and shape. Some are icosahedral (20 sides) others are filamentous. The head or capsid is composed of many copies of one or more different proteins. Inside the head is found the nucleic acid. The head acts as the protective covering for the nucleic acid. Many but not all phages have tails attached to the phage head. The tail is a hollow tube through which the nucleic acid passes during infection. The size of the tail can vary, and some phages do not even have a tail structure. In the more complex phages like T4 the tail is surrounded by a contractile sheath which contracts during infection of the bacterium. At the end of the tail, the more complex phages like T4 have a base plate and one or more tail fibers attached to it. The base plate and tail fibers are involved in the binding of the phage to the bacterial cell. Not all phages have base plates and tail fibers. In these instances, other structures are involved in binding of the phage particle to the bacterium. See Kutter and Sulakvelidze (2005) *Bacteriophages: Biology and Application*.

Bacteriophage Infect Bacteria

The first step in the infection process is the adsorption of the phage to the bacterial cell. This step is mediated by the tail fibers or by some analogous structure on those phages that lack tail fibers, and it is reversible. The tail fibers attach to specific receptors on the bacterial cell, and the host specificity of the phage (i.e., the bacteria that it is able to infect) is usually determined by the type of tail fibers that a phage has. The nature of the bacterial receptor varies for different bacteria (e.g., proteins on the outer surface of the bacterium, LPS, pili, and lipoprotein). These receptors are on the bacteria for other purposes, and phage have evolved to use these receptors for infection. See Kutter and Sulakvelidze (2005) *Bacteriophages: Biology and Application*.

The attachment of the phage to the bacterium via the tail fibers is a weak one and is reversible. Irreversible binding of phage to a bacterium is mediated by one or more of the components of the base plate. Phages lacking base plates have other ways of becoming tightly bound to the bacterial cell.

The irreversible binding of the phage to the bacterium results in the contraction of the sheath (for those phages which have a sheath), and the hollow tail fiber is pushed through the bacterial envelope. Phages that do not have contractile sheaths use other mechanisms to get the phage particle through the bacterial envelope. Some phages have enzymes that digest various components of the bacterial envelope. See also McGrath and van Sinderen (2007) *Bacteriophage: Genetics and Molecular Biology*.

Lytic (Virulent) Phage Life Cycle

Lytic or virulent phages are phages which can only multiply on bacteria and kill the cell by lysis at the end of the life cycle.

During the eclipse phase, no infectious phage particles can be found either inside or outside the bacterial cell. The phage nucleic acid takes over the host biosynthetic machinery, and phage specified mRNAs and proteins are made. There is an orderly expression of phage directed macromolecular synthesis, just as one sees in animal virus infections. Early mRNAs code for early proteins that are needed for phage DNA synthesis and for shutting off host DNA, RNA and protein biosynthesis. After phage DNA is made, late mRNAs and late proteins are made. The late proteins are the structural proteins that comprise the phage as well as the proteins needed for lysis of the bacterial cell. See also McGrath and van Sinderen (2007) *Bacteriophage: Genetics and Molecular Biology*.

In the Intracellular Accumulation Phase, the nucleic acid and structural proteins that have been made are assembled and infectious phage particles accumulate within the cell.

During the Lysis and Release Phase, the bacteria begin to lyse due to the accumulation of the phage lysis protein, and intracellular phage are released into the medium. The number of particles released per infected bacteria may be as high as 1000.

A common assay for lytic phage is the plaque assay where lytic phage are enumerated by a plaque assay. A plaque is a clear area which results from the lysis of bacteria. Each plaque arises from a single infectious phage. The infectious particle that gives rise to a plaque is called a pfu (plaque forming unit). See Kutter and Sulakvelidze (2005) *Bacteriophages: Biology and Application*.

Lysogenic (Temperate) Phage Life Cycle

Lysogenic or temperate phages are those that can either multiply via the lytic cycle or enter a quiescent state in the cell. In this quiescent state most of the phage genes are not transcribed; the phage genome exists in a repressed state. The phage DNA in this repressed state is called a prophage because it is not a phage but it has the potential to produce phage. In most cases the phage DNA actually integrates into the host chromosome and is replicated along with the host chromosome and passed on to the daughter cells. The cell harboring a prophage is not adversely affected by the presence of the prophage, and the lysogenic state may persist indefinitely. The cell harboring a prophage is termed a lysogen. See also McGrath and van Sinderen (2007) *Bacteriophage: Genetics and Molecular Biology*, herein incorporated by reference in its entirety.

Anytime a lysogenic bacterium is exposed to adverse conditions, the lysogenic state can be terminated. This process is called induction. Adverse conditions which favor the termination of the lysogenic state include desiccation, exposure to UV or ionizing radiation, and exposure to mutagenic chemicals. This leads to the expression of the phage genes, reversal of the integration process, and lytic multiplication. See Kutter and Sulakvelidze (2005) Bacteriophages: *Biology and Application, herein incorporated by reference in its entirety*.

At the time bacteriophages were discovered, with the age of antibiotics still in the future, bacteriophages were considered to be a potentially powerful cure for bacterial infections, and they were therapeutically utilized throughout the world during the pre-antibiotic era. The use of phages in humans was found to be very safe; however, phage therapy did not always work and, with the advent of antibiotics that were effective against a broad spectrum of pathogenic bacteria, it gradually fell out of favor in the United States and Western Europe. Several factors, including the lack of a broad understanding of phage biology, the "Soviet Taint," and inadequate diagnostic bacteriology techniques, contributed to the failure of some of the early phage therapy studies and to the associated decline of interest in phage therapy in the West. Reviewed in more detail in Sulakvelidze, et al. (2001) *Antimicrob Agents Chemother* 45(3): 649-659 and Summers (2001) *Ann Rev Microbiol* 55: 437-51. At the same time, phage therapy continued to be utilized in the former Soviet Union and Eastern Europe, where phage therapy still is being used to treat a wide range of bacterial diseases ranging from intestinal infections to septicemia. Comprehensive information about human and veterinary applications of bacteriophages has been recently reviewed by several investigators. See, e.g., Alisky, et al. (1998) *J Infect* 36(1): 5-15; Summers (2001) *Annu Rev Microbiol* 55: 437-51; Merril, et al. (2003) *Nat Rev Drug Discov* 2(6): 489-497; Sulakvelidze & Barrow (2005) "Phage therapy in animals and agribusiness. Bacteriophages: Biology and Applications." CRC Press: 335-380; Sulakvelidze & Kutter (2005). Bacteriophage therapy in humans. Bacteriophages: Biology and Application. CRC Press: 381-436.

Despite the use of bacteriophage in various practical settings, including the treatment of diseases in various animals, there remains in the art a need for the discovery of novel bacteriophages, selection of optimal bacteriophages for specific practical applications, and identifying methods for using these bacteriophages in several critical areas, including clinical applications, food safety-related uses and environmental decontamination. For example, one significant need concerns the treatment of processed or unprocessed food products to reduce, eliminate or prevent colonization with undesirable bacteria such as pathogens responsible for food-borne illness and food spoilage organisms. A second critical area of need concerns the removal of undesirable bacteria from industrial environments such as food processing facilities to prevent colonization thereof. A third critical area of need concerns the removal of antibiotic resistant organisms from environments where they may be passed to susceptible humans and animals, such as hospitals, nursing homes, veterinary facilities, and other such environments. Additionally, new bacteriophage and methods of using the same are needed for the prevention or treatment of animal and human bacterial disease, particularly those diseases caused by antibiotic-resistant organisms. Finally, bacteriophage compositions may be used a probiotics (e.g., the bacteriophage lyse undesirable bacteria leaving desirable microflora intact).

SUMMARY OF THE INVENTION

The invention meets the described needs and more by providing compositions comprising alone or in any combination novel LMSP-25, LMTA-34, LMTA-57, LMTA-94, or LMTA-148 bacteriophages having lytic specificity for the Targeted Bacteria. The invention additionally provides methods of using the Deposited Bacteriophages to control or prevent the infection or colonization of processed and unprocessed food products by Targeted Bacteria, or colonization of equipment involved in the processing of the same food product(s). The invention additionally provides methods of using the Deposited Bacteriophages to prevent, eradicate, or reduce the levels of colonization of various animals (including humans) with Targeted Bacteria. The invention also provides methods of detecting the presence of Targeted Bacteria cells on processed or unprocessed food products, or equipment involved in the processing of the same food products. The invention additionally provides methods of using the Deposited Bacteriophages for the removal of antibiotic-resistant or other undesirable pathogens from medical, veterinary, animal husbandry, and other environments where they may be passed to humans or animals. The invention additionally provides for methods of using the Deposited Bacteriophages to prevent or treat human and/or other animal diseases caused by Targeted Bacteria.

The Deposited Bacteriophage has binding specificity for Targeted Bacteria (i.e., *Listeria* species and strains), and is capable of lysing Targeted Bacteria (i.e., lytic bacteriophage). The invention also contemplates progeny, variants, substantially equivalent bacteriophages, and bacteriophage derivative(s) of the Deposited Bacteriophage.

In another embodiment, the variants of the Deposited Bacteriophage have the same phenotypic characteristics as the Deposited Bacteriophage. In another embodiment, the variants of the Deposited Bacteriophage have the same lytic specificity for *Listeria* as the Deposited Bacteriophage.

In a further embodiment, the variants of the Deposited Bacteriophage differ genetically from the Deposited Bacteriophage by a single genetic event including but not limited to silent mutations, inversions, deletions, insertions, polymorphisms, or point mutations but still retain the same phenotypic characteristics and lytic specificity for *Listeria* as the Deposited Bacteriophage.

In one embodiment, progeny are variants of the Deposited Bacteriophage.

In one embodiment, the invention provides progeny of the Deposited Bacteriophage having minor variation(s) in the genomic sequence and polypeptides encoded thereby while retaining the same general genotypic and/or phenotypic characteristics as the Deposited Bacteriophage. In particular these progeny are the result of successive passaging of the Deposited Bacteriophage where the variants accumulate silent mutations, conservative mutations, minor deletions, and/or minor replications of genetic material. The progeny described herein of the Deposited Bacteriophage retain the phenotypic characteristics of the Deposited Bacteriophage, in a preferred embodiment, the progeny retain lytic activity against the Target Bacteria.

In one embodiment, the invention provides variants of the Deposited Bacteriophage having minor variation(s) in the genomic sequence and polypeptides encoded thereby while retaining the same general genotypic and/or phenotypic characteristics as the Deposited Bacteriophage. In particular these variants can be the result of successive passaging of the Deposited Bacteriophage where the variants accumulate silent mutations, conservative mutations, minor deletions, and/or minor replications of genetic material. The variants described herein of the Deposited Bacteriophage retain the phenotypic characteristics of the Deposited Bacteriophage, in a preferred embodiment, the variants retain lytic activity against the Target Bacteria.

In one embodiment, the invention provides derivatives of the Deposited Bacteriophage comprising substances that constitute subunits or expression products of the Deposited bacteriophage or its progeny, including (but not limited to) phage nucleic acids, partial or complete phage genes, gene expression products, and structural components (e.g., polyribonucleotide(s) and polydeoxyribonucleotide(s), including modified or unmodified bacteriophage DNA, cDNA, mRNA and synthetic polynucleotide sequences, as well as DNA/RNA hybrids.) In another embodiment, the invention provides modified polynucleotides (e.g., phosphorylated DNAs) of the Deposited Bacteriophages.

In one embodiment, the invention provides the use of the Deposited Bacteriophage, and its progeny and derivatives, to control the growth on, or colonization of, processed and unprocessed food products by Targeted Bacteria, or the colonization of buildings and equipment, particularly those associated with the processing of the same food product. The invention also provides methods of identifying Targeted Bacteria as a bacterial diagnostic and/or detecting the presence of Targeted Bacteria on processed or unprocessed food products, or equipment or buildings such as those involved in the processing of the same food products. The invention further provides methods of using the Deposited Bacteriophage for the removal of antibiotic-resistant or other undesirable pathogens from medical, veterinary, animal husbandry, or any additional environments where they may be passed to humans or animals. The invention additionally provides for methods of using the Deposited Bacteriophage to prevent and/or treat human and animal diseases caused by Targeted Bacteria. The Deposited Bacteriophage is administered for the methods of the invention as a homogenous phage administration, or alternatively as a component of a multi-phage composition comprising several bacteriophages. These methods of use are provided with greater particularity infra.

In one embodiment, one possessing the Deposited Bacteriophage will inevitably be in possession of progeny of the Deposited Bacteriophages. Furthermore, after successive subculturing (e.g., over 50 passages) of the Deposited Bacteriophages, progeny having genetic variations within the scope of "closely related" organisms, as descried by Tenover, are present.

In one embodiment, the invention comprises bacteriophages substantially equivalent to the Deposited Bacteriophages—bacteriophages that are "indistinguishable" from or "closely related" to the Deposited Bacteriophages as these terms are defined in Tenover.

In one embodiment, the composition comprises at least one, two, three, four, or five of the Deposited Bacteriophages.

In another embodiment, a probiotic composition may comprise at least one of the Deposited Bacteriophages. The probiotic composition may further comprise an excipient, carrier, stabilizer, flavoring, or colorant agent.

In another embodiment, the composition comprises at least one the Deposited Bacteriophage and additionally comprising a washing step in which the food product is contacted with an aqueous medium to remove the bacteriophage composition.

The present invention is directed to novel phage compositions useful in treating food products to minimize or eliminate bacterial contamination by *Listeria* bacteria. The phage compositions can be formulated with suitable carriers.

The compositions of the present invention may be used for human, veterinary, agricultural or aquacultural purposes. Furthermore, the compositions as described herein may be used for treatment of trees and plants, and environmental applications. The composition may be used within a cream, lotion or gel, be admixed with a pharmaceutical carrier and administered topically, orally, nasally, used as a powdered inhalant, or the antibacterial composition may be added to a feed for animal, aquatic or avian uses.

In another embodiment of the invention, isolated progeny of the deposited bacteriophage derived from the deposited bacteriophage.

In another embodiment of the invention, isolated progeny of the deposited bacteriophage derived from bacteriophages derived from the deposited bacteriophage.

Another embodiment of the invention comprises isolated progeny of the progeny of the deposited bacteriophage.

One embodiment of the invention comprises at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

Another embodiment of the invention comprises at least one isolated progeny of bacteriophage LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

Another embodiment is a composition comprises at least one isolated bacteriophage LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

Another embodiment is a composition comprises at least one progeny of bacteriophage LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

Still another embodiment comprises at least one derivative of the bacteriophage of isolated bacteriophage LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains, said derivative comprising nucleic acids, partial or complete genes, gene expression products, structural components, or one or more combinations thereof.

Another embodiment comprises at least one derivative of the progeny bacteriophage of isolated bacteriophage LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains, said derivative comprising nucleic acids, partial or complete genes, gene expression products, structural components, or one or more combinations thereof.

One embodiment comprises a method for the prevention of food borne illnesses caused by *Listeria* strains, comprising contacting a food product or products with a microbial growth inhibiting effective amount of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

One embodiment comprising a method for the reduction of the incidence of food borne illnesses caused by *Listeria* strains, comprising contacting a food product or products with a microbial growth inhibiting effective amount of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

In a more preferred embodiment, the contacting described in the methods herein comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

In another embodiment, a method for reducing the risk of bacterial infection or sepsis in a person colonized with bacteria comprising treating the colonized person with a pharmaceutical composition containing bacteriophage of one or more strains of the Deposited Bacteriophage which produce lyric infections in said bacteria, wherein said treatment occurs prior to said colonized person developing an illness due to said bacteria and said treatment reduces the risk of bacterial infection or sepsis in said colonized person, and wherein said treatment of the colonized person reduces the level of colonization with bacteria susceptible to the bacteriophage by at least one log, wherein said composition is administered intravesicularly, topically, orally, rectally, ocularly, optically, nasally, or via inhalation. Additionally, said bacteria is *Listeria*. In a more preferred embodiment, the bacteriophage composition is an oral tablet, capsule or liquid, a nasal aerosol, a throat wash, a mouth wash or gargle, a toothpaste, and a topical ointment. In another embodiment, the colonized person is a person having a wound selected from the group consisting of an ulcer, a laceration, a deep penetrating wound and a surgical wound, and the bacteriophage produce lytic infections in bacteria capable of infecting these wounds.

In another embodiment of the invention, a composition comprising at least one of the Deposited Bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains. In another embodiment, the composition further comprises a pharmaceutically acceptable carrier wherein the pharmaceutically acceptable carrier is an aerosol, a paste, a powder, or an injectable formulation.

Another embodiment comprises the use of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains for the prevention of food borne illnesses caused by *Listeria* strains comprising contacting a food product or products with a microbial growth inhibiting effective amount of said bacteriophage composition. In a preferred embodiment, said contacting comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

Still another embodiment comprises the use of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains for the reduction of the incidence of food borne illnesses caused by *Listeria* strains comprising contacting a food product or products with a microbial growth inhibiting effective amount of said bacteriophage composition. In a preferred embodiment, said contacting comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

Another embodiment comprises the use of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains for the prevention of food borne illnesses caused by *Listeria* strains, comprising contacting a food product or products with a microbial growth inhibiting effective amount of said bacteriophage composition. In a preferred embodiment, said contacting comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

In a preferred embodiment comprises the use of a bacteriophage composition comprising at least one of the isolated bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains for the reduction of the incidence of food borne illnesses caused by *Listeria* strains comprising contacting a food product or products with a microbial growth inhibiting effective amount of said bacteriophage composition In a preferred embodiment, said contacting comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

In a more preferred embodiment, the compositions are pharmaceutical compositions.

In a preferred embodiment, the compositions comprising at least one, two, three, four, five, six, or seven of the Deposited Bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

In a still more preferred embodiment, the Deposited Bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, have lytic activity against *Listeria* strains, wherein said *Listeria* strains are *Listeria* strains.

In another embodiment, variants of the Deposited Bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, retain the phenotypic characteristics of said bacteriophage and wherein said bacteriophage and variants thereof have lytic activity against *Listeria* strains.

In another embodiment, progeny of the Deposited Bacteriophages LMSP-25, LMTA-34, LMTA-57, LMTA-94, or LMTA-148 deposited under ATCC accession No. PTA-8353, PTA-8354, PTA-8355, PTA-8356, or PTA-8357, respectively, and variants thereof which retain the phenotypic characteristics of said bacteriophage and wherein said bacteriophage and variants thereof retains lytic activity against *Listeria* strains.

In another embodiment of the invention, isolated capsid of the Deposited Bacteriophage.

Another embodiment of the invention, isolated nucleic acid of the Deposited Bacteriophage comprising the phage genome.

BRIEF DESCRIPTION OF THE FIGURES

FIG. 1 shows a Restriction Fragment Length Polymorphism (RFLP) profile of the *Listeria* bacteriophages.

DETAILED DESCRIPTION OF EMBODIMENTS OF THE INVENTION

Definitions

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, "about," as used herein when referring to a measurable value such as an amount of a compound, dose, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this invention belongs.

"Administration," as used herein, refers broadly to any means by which a composition is given to a patient.

"ATCC," as used herein, refers to the American Type Culture Collection, located at 10801 University Boulevard, Manassas, Va., 20110-2209, USA.

"Bacteriophage composition," as used herein refers broadly to a composition comprising, or alternatively consisting essentially of, or alternatively consisting of, the Deposited Bacteriophage. A "bacteriophage composition" as used herein does not include the Deposited Bacteriophage as it exists in its natural environment prior to isolation and/or substantial purification. Further, a composition may comprise, consist of, or essentially consist of at least one of the Deposited Bacteriophages. Alternatively, the compositions as described herein may comprise, consist of, or essentially consist of at least one, two, three, four, five, or all six of the Deposited Bacteriophages.

"Bacteriophages substantially equivalent to the Deposited Bacteriophages," as used herein, refers broadly to those bacteriophages that are "indistinguishable" from or "closely related" to the Deposited Bacteriophages as these terms are defined in Tenover, F. C. et al. (1995) "Interpreting Chromosomal DNA Restriction Patterns Produced by Pulsed-Field Gel Electrophoresis: Criteria for Bacterial Strain Typing." *J. Clin. Microbiol.* 33: 2233-2239. Tenover describes that organisms are "genetically indistinguishable if their restriction patterns have the same numbers of bands and the corresponding bands are the same apparent size." Tenover at page 2235. Epidemiologically, these organisms are "all considered to represent the same strain; i.e., isolates demonstrating the common outbreak pattern represent the outbreak strain." Tenover at page 2235. Accordingly, under Tenover, a particular organism is "indistinguishable" from itself or its clone. Tenover describes that an organism is "closely related" if its "PFGE pattern differs from the outbreak pattern by changes consistent with a single genetic event, i.e., a point mutation or an insertion or deletion of DNA. Such changes typically result in two to three band differences." Tenover at page 2235. Tenover states that such two to three band differences "have been observed in strains of some species when they are cultured repeatedly over time or isolated multiple times from the same patient." Tenover at page 2235. Accordingly, under Tenover, progeny of a organism (e.g., descendants of the organism created by serial passage of the organism), for example, are "closely related" to the parent organism.

"Colonization" or "colonized," as used herein, refers broadly to the presence of Targeted Bacteria on foodstuff(s), or environmental surface(s), or in vivo such as in the gastrointestinal tract or skin of a mammalian organism without perceptible significant alteration other than the presence of bacteria. The terms "colonization" and "colonized" stand in contrast to the terms "infection" or "infected" which are commonly understood to require perceptible deleterious alteration as part of their definition. "Colonization" and "colonized" may also refer to the presence of bacteria in or on a human or animal without perceptible damage, alteration, or disease.

"Deposited Bacteriophage," as used herein, refers broadly to isolated bacteriophages LMSP-25 deposited with the ATCC on Apr. 19, 2007, and receiving ATCC Deposit Accession No. PTA-8353, LMTA-34 deposited with the ATCC on Apr. 19, 2007, and receiving ATCC Deposit Accession No. PTA-8354, LMTA-57 deposited with the ATCC on Apr. 19, 2007 and receiving ATCC Deposit Accession No. PTA-8355, LMTA-94 deposited with the ATCC on Apr. 19, 2007, and receiving ATCC Deposit Accession No. PTA-8356, and LMTA-148 deposited with the ATCC on Apr. 19, 2007, and receiving ATCC Deposit Accession No. PTA-8357, said bacteriophage having lytic activity against *Listeria* strains, and variants thereof, wherein said variants retain the phenotypic characteristics of said bacteriophage and wherein said bacteriophage and variants thereof have lytic activity against *Listeria* strains. All of the Deposited Bacteriophages described herein are lytic not lysogenic phages. The Deposited Bacteriophages have lytic activity against *Listeria* strains.

The isolated bacteriophages identified by internal laboratory designations LMSP-25, LMTA-34, LMTA-57, LMTA-94, and LMTA-148 were deposited under the terms of the Budapest Treaty on Jan. 10, 2012, and given the ATCC Deposit Accession Nos. PTA-8353, PTA-8354, PTA-8355, PTA-8356, and PTA-8357 by the American Type Culture Collection (ATCC) at 10801 University Blvd., Manassas, Va. 20110. The isolated bacteriophages identified by internal laboratory designations LMSP-25, LMTA-34, LMTA-57, LMTA-94, and LMTA-148 were deposited under the terms of the Budapest Treaty on Apr. 19, 2007, and given the ATCC Deposit Accession Nos. PTA-8353, PTA-8354, PTA-8355, PTA-8356, and PTA-8357 by the American Type Culture Collection (ATCC) at 10801 University Blvd., Manassas, Va. 20110. Access to these deposits will be available during the pendency of the application to the Commissioner of Patents and Trademarks and persons determined by the Commissioner to be entitled thereto upon request. The deposits will be maintained for a period of 30 years, or 5 years after the most recent request, or for the enforceable life of the patent, whichever is longer, and will be replaced if it becomes nonviable during that period.

"Derivatives," as used herein, refers broadly to all substances that constitute subunits or expression products of the Deposited Bacteriophage or its progeny, including (but not limited to) phage nucleic acids, partial or complete phage genes, gene expression products, and structural components. For example, derivatives of the invention mean polyribonucleotide(s) and polydeoxyribonucleotide(s), including modified or unmodified bacteriophage DNA, cDNA, mRNA and synthetic polynucleotide sequences, as well as DNA/RNA hybrids. Polynucleotides of the invention also encompass modified polynucleotides, such as for example phosphorylated DNAs.

"Effective amount," as used herein, refers broadly to the amount of an isolated bacteriophage that, when administered to a patient for treating a disease, is sufficient to effect such treatment for the disease. The effective amount can be an amount effective for prophylaxis, and/or an amount effective for prevention. The effective amount can be an amount effective to reduce the incidence of food borne illnesses, an amount effective to prevent incidence of food borne illnesses, to reduce the severity of infection, to eliminate infection, to slow the development of the infection, to prevent the development of infection (colonization). The "effective amount" can vary depending on the disease and its severity and the age, weight, medical history, predisposition to conditions, preexisting conditions, of the patient to be treated. The term "effective amount" is taken to be synonymous with "therapeutically effective amount" for purposes of this invention.

"Isolated," as used herein, refers broadly to material removed from its original environment in which it naturally occurs, and thus is altered by the hand of man from its natural environment. Isolated material may be, for example, foreign nucleic acid included in a vector system, foreign nucleic acid contained within a host cell, or any material which has been removed from its original environment and thus altered by the hand of man. Isolated material further encompasses bacteriophage specific for the Targeted Bacteria or particular Targeted Bacteria isolates, isolated and cultured separately from the environment in which it was located, where these isolates are present in purified compositions that do not contain any significant amount of other bacteriophage or bacterial strains, respectively.

"Mammal" as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, chimpanzees, chinchillas, cattle, dogs, goats, gorillas, horses, humans, lemurs, llamas, mice, non-human primates, pigs, rats, sheep, shrews, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C., which is hereby incorporated by reference.

"ORF," as used herein, refers broadly to an Open Reading Frame which is an in-frame sequence of codons that (in view of the genetic code) correspond to or encode a protein or peptide sequence. Two ORFs correspond to each other if the sequences or their complementary sequences encode the same amino acid sequences. An ORF sequence, operably associated with appropriate regulatory sequences, may be transcribed and translated into a polypeptide in vivo. A polyadenylation signal and transcription termination sequence will usually be located 3' to the coding sequence.

"Patient" as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient can be a clinical patient such as a human or a veterinary patient such as a companion, domesticated, livestock, exotic, or zoo animal. Animals can be mammals, reptiles, birds, amphibians, or invertebrates.

"Progeny," as used herein, refers broadly to replicates of the Deposited bacteriophage, including descendants of the Deposited bacteriophage created by serial passage of the Deposited bacteriophage or by other means well known in the art, or bacteriophage whose RFLP profiles are substantially equivalent to the RFLP profile of the Deposited bacteriophage (See FIGS. 1 and 2). The term substantially equivalent is used to describe variability between organisms in accordance with the standards advanced by Tenover et al. from the United States Centers for Disease Control and Prevention (Tenover, F. C. et al. (1995) Interpreting Chromosomal DNA Restriction Patterns Produced by Pulsed-Field Gel Electrophoresis: Criteria for Bacterial Strain Typing. J. Clin. Microbiol. 33:2233-2239). Tenover teaches the acceptable levels of variation that may be seen when the genomes of identical propagated organisms are electrophoretically analyzed following restriction enzyme digestion. Bacteriophages "substantially equivalent" to the Deposited Bacteriophages are "indistinguishable" from or "closely related" to the Deposited Bacteriophages. Tenover describes a system for interpreting chromosomal DNA Restriction Enzyme digest patterns ("RFLP") using Pulsed-Field Gel Electrophoresis (PFGE). Tenover at page 2233. In particular, Tenover sets forth various categories of genetic and epidemiologic relatedness including those organisms that are "indistinguishable" from or "closely related" to each other. While Tenover provides a schematic (prophetic) example of PFGE patterns of genetically related bacteria, the same principles being applied for bacteria also apply to bacteriophage, because Tenover is analyzing genomic DNA.

"Recombinant bacteriophage," as used herein, refers broadly to all genetically modified versions of the Deposited Bacteriophage or its progeny, obtained by serial passaging (in vivo or in vitro) or genetic manipulations of the Deposited Bacteriophage or its progeny. Such manipulations include, but are not limited to, introducing genes or gene cassettes encoding alternative proteins or nonfunctional proteins, or noncoding nucleotide sequences into the genome of the Deposited Bacteriophage.

"Substantially pure," as used herein refers broadly to material essentially free of any similar macromolecules that would normally be found with it in nature. For example, a substantially pure bacteriophage is in a composition that contains no more than 1% of other bacteriophages.

"Targeted Bacteria," as used herein, refers broadly to *Listeria* species including but not limited to *Listeria monocytogenes* spp. (including serotypes 1/2a, 1/2b, and 4b).

"Therapy" or "therapeutic," as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, regimen, remedy, minimization, reduction, alleviation, and/or providing relief from a disease, signs, and/or symptoms of a disease. Therapy encompasses an alleviation of signs and/or symptoms in patients with ongoing disease signs and/or symptoms, e.g. of infection. Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms, e.g. of colonization. Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease.

"Variants," as used herein, refers broadly to bacteriophages that share the same phenotypic characteristics of the Deposited Bacteriophage and share the same lytic activity of the Deposited Bacteriophages against the Targeted Bacteria. Variants also include bacteriophages that are "substantially equivalent" to the Deposited Bacteriophages, or are "indistinguishable" from or "closely related" to the Deposited Bacteriophages as described in Tenover.

The Deposited Bacteriophage

The Deposited Bacteriophages have binding specificity for Targeted Bacteria, and are capable of lysing Targeted Bacteria. The invention further contemplates variants of the Deposited Bacteriophage, which are bacteriophage having minor variation(s) in the genomic sequence and polypeptides encoded thereby while retaining the same general genotypic and phenotypic characteristics as the Deposited Bacteriophage. Such variants are considered to be the Deposited Bacteriophages in accordance with the standards advanced by Tenover from the United States Centers for Disease Control and Prevention (Tenover, et al. (1995) "Interpreting Chromosomal DNA Restriction Patterns Produced by Pulsed-Field Gel Electrophoresis Criteria for Bacterial Strain Typing." *J. Clin. Microbiol.* 33: 2233-2239). The invention also contemplates progeny and bacteriophage derivative(s). The progeny, variants, substantially equivalent bacteriophages, and bacteriophage derivative(s) of the Deposited Bacteriophage all retain the same target specificity (e.g., the Target Bacteria) and are lytic phages.

The invention as described herein pertains to the Deposited Bacteriophages. The invention as described herein also pertains to progeny of the Deposited Bacteriophages and teaches RFLP methods for identifying progeny and other "substantially equivalent" bacteriophages. RFLP analysis is a means of identifying closely related bacteriophages. See e.g., Schnabel and Jones (January 2001) "Isolation and Characterization of Five *Erwinia anylovora* Bacteriophages and Assessment of Phage Resistance in Strains of *Erwinia amylovora.*" *Applied and Environmental Microbiology* 67(1): 59-64 and Osawa, et al. (2000) "Genotypic variations of Shiga toxin-converting phages from enterohaemorrhagic *Escherichia coli* isolates." *J. Med. Microbiol.* 49: 565-574.

Using methods and materials known in the art, a person of skill in art in possession of the Deposited Bacteriophage, will inevitably be in possession of progeny of the Deposited Bacteriophages. Indeed, after successive subculturing of the Deposited Bacteriophages, progeny having genetic variations within the scope of "closely related" organisms, as described by Tenover, are present. Furthermore, again only relaying on methods and materials known in the art, a person of skill in the art in possession of the Deposited Bacteriophage will able to isolated and identify variants of the Deposited Bacteriophages as described herein. In particular, the variants of the Deposited Bacteriophage having minor variation(s) in the genomic sequence and polypeptides encoded thereby while retaining the same general genotypic and/or phenotypic characteristics as the Deposited Bacteriophage. Such variants are considered to be the Deposited Bacteriophage in accordance with the standards advanced by Tenover. In particular these variants may be the result of successive passaging of the Deposited Bacteriophage where the variants accumulate silent mutations, conservative mutations, minor deletions, and/or minor replications of genetic material. The variants described herein of the Deposited Bacteriophage retain the phenotypic characteristics of the Deposited Bacteriophage, in a preferred embodiment, the variants have lytic activity against the Target Bacteria.

Furthermore, bacteriophages substantially equivalent to the Deposited Bacteriophages are those bacteriophages that are "indistinguishable" from or "closely related" to the Deposited Bacteriophages. See Tenover at page 2235. Accordingly, under Tenover, progeny of an organism (e.g., descendants of the organism created by serial passage of the organism), for example, are "closely related" to the parent organism.

Additionally, the Deposited Bacteriophages can be used to isolate derivatives, in particular all substances that constitute subunits or expression products of the Deposited bacteriophage or its progeny, including (but not limited to) phage nucleic acids, partial or complete phage genes, gene expression products, and structural components. For example, derivatives of the invention mean polyribonucleotide(s) and polydeoxyribonucleotide(s), including modified or unmodified bacteriophage DNA, cDNA, mRNA and synthetic polynucleotide sequences, as well as DNA/RNA hybrids. Polynucleotides of the invention also encompass modified polynucleotides, such as for example phosphorylated DNAs. Depending upon the phage, the nucleic acid can be either DNA or RNA but not both and it can exist in various forms. Further, the nucleic acids of phages often contain unusual or modified bases. These modified bases protect phage nucleic acid from nucleases that break down host nucleic acids during phage infection. The size of the nucleic acid varies depending upon the phage. The phages can have only enough nucleic acid to code for 3-5 average size gene products while the some phages may code for over 100 gene products.

Additionally, the Deposited Bacteriophage comprises an isolated bacteriophage LMSP-25, LMTA-34, LMTA-57, LMTA-94, or LMTA-148, deposited under ATCC Accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

The Deposited Bacteriophage also comprises isolated progeny of bacteriophage LMSP-25, LMTA-34, LMTA-57, LMTA-94, or LMTA-148, deposited under ATCC Accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

Additionally, the Deposited Bacteriophage comprises an isolated bacteriophage substantially equivalent to the bacteriophage LMSP-25, LMTA-34, LMTA-57, LMTA-94, or LMTA-148, deposited under ATCC Accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

The Deposited Bacteriophage also comprises isolated progeny of bacteriophage substantially equivalent to the bacteriophage LMSP-25, LMTA-34, LMTA-57, LMTA-94, or LMTA-148, deposited under ATCC Accession No. PTA-8353, PTA-8354, PTA-8355, PTA-8356, or PTA-8357, respectively, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

The Deposited Bacteriophages LMSP-25, LMTA-34, LMTA-57, LMTA-94, or LMTA-148, deposited under ATCC Accession No. PTA-8353, PTA-8354, PTA-8355, PTA-8356, or PTA-8357, respectively, respectively, have lytic activity against *Listeria* strains, wherein variants retain the phenotypic characteristics of said bacteriophage and wherein said bacteriophage and variants thereof have lytic activity against *Listeria* strains.

The Deposited Bacteriophage also encompasses progeny of the Deposited Bacteriophages LMSP-25, LMTA-34, LMTA-57, LMTA-94, or LMTA-148, deposited under ATCC Accession No. PTA-8353, PTA-8354, PTA-8355, PTA-8356, or PTA-8357, respectively, respectively, and variants thereof which retain the phenotypic characteristics of said bacteriophage and wherein said bacteriophage and variants thereof have lytic activity against *Listeria* strains.

The Deposited Bacteriophages also comprise bacteriophages substantially equivalent to the bacteriophage LMSP-25, LMTA-34, LMTA-57, LMTA-94, or LMTA-148, deposited under ATCC Accession No. PTA-8353, PTA-8354, PTA-8355, PTA-8356, or PTA-8357, respectively, respectively, have lytic activity against *Listeria* strains, wherein variants retain the phenotypic characteristics of said bacteriophage and wherein said bacteriophage and variants thereof have lytic activity against *Listeria* strains.

The Deposited Bacteriophage also encompasses progeny substantially equivalent to the Deposited Bacteriophages LMSP-25, LMTA-34, LMTA-57, LMTA-94, or LMTA-148, deposited under ATCC Accession No. PTA-8353, PTA-8354, PTA-8355, PTA-8356, or PTA-8357, respectively, respectively delete, and variants thereof which retain the phenotypic characteristics of said bacteriophage and wherein said bacteriophage and variants thereof have lytic activity against *Listeria* strains.

Use of the Deposited Bacteriophages and their Progeny Compositions

The invention contemplates the use of the Deposited Bacteriophage, and its progeny and derivatives, to control the growth on, or colonization of, processed and unprocessed food products by Targeted Bacteria, or the colonization of buildings and equipment, particularly those associated with the processing of the same food product. The invention also provides methods of identifying Targeted Bacteria as a bacterial diagnostic and/or detecting the presence of Targeted Bacteria on processed or unprocessed food products, or equipment or buildings such as those involved in the processing of the same food products.

The invention further provides methods of using the Deposited Bacteriophages for the removal of antibiotic-resistant or other undesirable pathogens from medical, veterinary, animal husbandry, or any additional environments where they may be passed to humans or animals. The invention additionally provides for methods of using the Deposited Bacteriophages to prevent and/or treat human and animal diseases caused by Targeted Bacteria. The Deposited Bacteriophages are administered for the methods of the invention as a homogenous phage administration, or alternatively as a component of a multi-phage composition comprising several bacteriophages. These methods of use are provided with greater particularity infra.

According to this invention, the Deposited Bacteriophage are formulated in compositions containing the bacteriophage and a carrier, and can be stored as a concentrated aqueous solution or lyophilized powder preparation. Bacteriophage may be formulated by resuspending purified phage preparation in aqueous medium, such as deionized water, buffer solution (e.g., Tris-HCl pH 7.4), mineral water, 5% sucrose solution, glycerol, dextran, polyethylene glycol, sorbitol, or other formulations that maintain phage viability, and are non-toxic to humans. Suitable formulations, wherein the carrier is a liquid, for administration (e.g., a nasal spray or as nasal drops, include aqueous or oily solutions of the active ingredient.)

A spray comprising a composition of the present invention can be produced by forcing a suspension or solution of a compound disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

According to this invention, the Deposited Bacteriophage are preferably formulated in pharmaceutical compositions containing the bacteriophage and a pharmaceutically acceptable carrier, and can be stored as a concentrated aqueous solution or lyophilized powder preparation. Bacteriophage may be formulated for oral administration by resuspending purified phage preparation in aqueous medium, such as deionized water, mineral water, 5% sucrose solution, glycerol, dextran, polyethylene glycol, sorbitol, or such other formulations that maintain phage viability, and are non-toxic to humans. Alternatively, the pharmaceutical composition can further comprise an adjuvant. The pharmaceutical composition may contain other components so long as the other components do not reduce the effectiveness (ineffectivity) of the bacteriophage so much that the therapy is negated. Pharmaceutically acceptable carriers are well known, and one skilled in the pharmaceutical art can easily select carriers suitable for particular routes of administration (Remington's Pharmaceutical Sciences, Mack Publishing Co., Easton, Pa., 1985).

The pharmaceutical compositions containing Deposited Bacteriophage may be administered by parenteral (subcutaneously, intramuscularly, intravenously, intraperitoneally, intrapleurally, intravesicularly or intrathecally), topical, oral, rectal, inhalation, ocular, optic, or nasal route, as necessitated by choice of drug and disease.

The invention provides a pharmaceutical composition comprising at least one of the Deposited Bacteriophages, progeny, and/or variants thereof and a pharmaceutical carrier.

The Deposited Bacteriophage(s) of the invention may be administered in a powdered form in combination with additional components. The additional components can include stabilizing agents, such as salts, preservatives and antibiotics. The additional components can include nutritive components, such as those used to make a nutrient broth as described herein, or other useful components as determined by one skilled in the art.

A pharmaceutical composition includes at least one Deposited Bacteriophage in combination with a pharmaceutically acceptable carrier. Examples of acceptable carriers include a solid, gelled or liquid diluent or an ingestible capsule. One or more of the bacteriophages of the invention, or a mixture thereof, may be administered orally in the form of a pharmaceutical unit dosage form comprising the bacteriophage in combination with a pharmaceutically acceptable carrier. A unit dosage of the bacteriophage may also be administered without a carrier material.

The pharmaceutical compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the bacteriophage(s) of the invention are released into the intestine after passing through the stomach.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The bacteriophages according to the invention may also be formulated for parenteral administration (e.g., by injection, for example, bolus injection or continuous infusion) and may be presented in unit dosage form in ampules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the bacteriophage(s) of the invention may be in powder form, obtained by lyophilization from solution, for constitution with a suitable vehicle, e.g., sterile saline, before use. Methods for use of bacteriophage in injectable form have been described. Merrill, et al. (1996) PNAS (USA) 93: 3188.

For topical administration to the epidermis, the bacteriophage(s) may be formulated as ointments, creams or lotions. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Pharmaceutical compositions suitable for topical administration in the mouth include unit dosage forms such as lozenges comprising a bacteriophage(s) of the invention in a flavored base, usually sucrose and acadia or tragacanth. Pastilles comprising one or more bacteriophages in an inert base such as gelatin and glycerin or sucrose and acacia are also provided. Mucoadherent gels and mouthwashes comprising a bacteriophage(s) of the invention in a suitable liquid carrier are additionally provided.

The present invention relates to stabilized bacteriophage formulations and their use as delivery systems. More particularly, the present invention pertains to stabilized bacteriophage formulations, methods for preparing stabilized bacteriophage formulations, and uses of stabilized bacteriophage formulations.

The present invention provides a method for producing a composition comprising, adsorbing an aqueous solution of bacteriophages, or phage components, onto a solid or powdered matrix to produce composition, and drying the composition to produce a composition.

The present invention also pertains to the method described above wherein the matrix may be selected from the group consisting of skim milk powder, soya protein powder, whey protein powder, albumin powder, casein, gelatin, single cell proteins, algal protein, plant peptone, trehalose, mannitol, powdered sugar, sugar alcohol, charcoal, latex beads, a water-soluble carbohydrate-based material, talc, chitin, and fish cartilage.

The present invention also provides a pharmaceutical composition comprising at least one Deposited Bacteriophage, or phage component, adsorbed onto a matrix.

The present invention includes the material as defined above, wherein the soluble matrix is selected from the group consisting of skim milk powder, soya protein, albumin powder, single cell proteins, trehalose, mannitol, sugar and sugar alcohol.

The compositions of the present invention are easy to prepare and exhibit the property of being stable over various lengths of time at refrigerator and room temperatures, from about $-10°$ C. to about $25°$ C.

Compositions of the present invention with little or no loss in titer. The antibacterial compositions of the present invention may be used within lotions, lubricants, gels and creams, toothpaste, be admixed with a pharmaceutically acceptable carrier for oral, nasal, or topical applications for example but not limited to skin, vaginal, ophthalmic, nasal, aural, anal, rectal, and other types of administration, or be used within wound dressings, and exhibit antimicrobial activity.

The present invention provides stabilized phage preparations in a dry form as a delivery system for powder inhalants. The present invention also provides a suitable matrix for preparing phage or phage compositions for encapsulation and delivery to the gut past the stomach acids.

Pharmaceutical compositions suitable for rectal administration are most preferably presented as unit dose suppositories. Suitable carriers include saline solution, nutrient broths, and other materials commonly used in the art. Pharmaceutical compositions suitable for vaginal administration may be presented as pessaries, tampons, creams, gels, pastes, foams or sprays that contain a carrier in addition to a bacteriophage. Such carriers are well known in the art.

For administration by inhalation, the bacteriophage(s) according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the bacteriophage(s) of the invention may take the form of a dry powder composition, for example, a powder mix of the bacteriophage(s) and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, the bacteriophage(s) of the invention may be administered via a liquid spray, such as via a plastic bottle atomizer. For topical administration to the eye, the bacteriophage(s) according to the invention can be administered as drops and gels.

Pharmaceutical compositions of the invention may also contain other adjuvants such as flavorings, colorings, antimicrobial agents, or preservatives. The invention also provides kits containing packaging and a bacteriophage(s) of the invention.

Dose and duration of therapy will depend on a variety of factors, including the patient age, patient weight, and tolerance of the phage. Bacteriophage may be administered to patients in need of the therapy provided by this invention by oral administration. Based on previous human experience in Europe, a dose of phage between $10^7$ and $10^{11}$ PFU will be suitable in most instances. The phage may be administered orally in, for example, mineral water, optionally with 2.0 grams of sodium bicarbonate added to reduce stomach acidity. Alternatively, sodium bicarbonate may be administered separately to the patient just prior to dosing with the phage. Phages also may be incorporated in a tablet or capsule which will enable transfer of phages through the stomach with no reduction of phage viability due to gastric acidity, and release of fully active phages in the small intestine. The frequency of dosing will vary depending on how well the phage is tolerated by the patient and how effective a single versus multiple dose is at reducing bacterial (e.g., *Listeria*) gastrointestinal colonization.

The dose of Deposited Bacteriophage and duration of therapy for a particular patient can be determined by the skilled clinician using standard pharmacological approaches in view of the above factors. The response to treatment may be monitored by, analysis of blood or body fluid levels of *Listeria*, or *Listeria* levels in relevant tissues or monitoring disease state in the patient. The skilled clinician will adjust the dose and duration of therapy based on the response to treatment revealed by these measurements.

One of the major concerns about the use of phages in clinical settings is the possible development of bacterial resistance against them. However, as with antimicrobial resistance, the development of resistance to phages takes time. The successful use of phages in clinical settings will require continual monitoring for the development of resistance, and, when resistance appears, the substitution of other phages to which the bacterial mutants are not resistant. In general, phage preparations may be constructed by mixing several separately grown and well-characterized lytic monophages, in order to (i) achieve the desired, broad target activity of the phage preparation, (ii) ensure that the preparation has stable lytic properties, and (iii) minimize the development of resistance against the preparation.

The development of neutralizing antibodies against a specific phage also is possible, especially after parenteral administration (it is less of a concern when phages are administered orally and/or locally). However, the development of neutralizing antibodies may not pose a significant obstacle in the proposed clinical settings, because the kinetics of phage action is much faster than is the host production of neutralizing antibodies. For example, phages will be used for just a few days, sufficient to reduce bacterial colonization during the time period when immunocompromised patients are most susceptible to the development of potentially fatal septicemia, but not long enough for phage-neutralizing antibodies to develop. If the development of antiphage antibodies is a problem, several strategies can be used to address this issue. For example, different phages having the same spectrum of activity (but a different antigenic profile) may be administered at different times during the course of therapy. On a more sophisticated level, therapeutic phages may be genetically engineered which will have a broad lytic range and/or be less immunogenic in humans and animals.

It will be appreciated that the amount of the present bacteriophages, required for use in treatment will vary not only with the particular carrier selected but also with the route of administration, the nature of the condition being treated and the age and condition of the patient. Ultimately the attendant health care provider may determine proper dosage.

Food Preservation

In one embodiment, the invention contemplates a method for the prevention of foodborne illnesses caused by the Targeted Bacteria, comprising contacting a food product or products intended for humans or animals with a microbial growth inhibiting effective amount of a bacteriophage composition comprising the Deposited Bacteriophage. The modes of contact include, but are not limited to, spraying or misting the Deposited Bacteriophages composition on the food product(s), or by dipping or soaking the food product(s) in a solution containing a concentration of the Deposited Bacteriophages sufficiently high to inhibit the growth of Targeted Bacteria, or adding, injecting or inserting the Deposited Bacteriophages into the food product(s).

In another embodiment, the invention contemplates the application of the Deposited Bacteriophages composition to equipment associated with the processing of food product(s), such as cutting instruments, conveyor belts, and any other implements utilized in the mass production of food products, including the preparation, storage and packaging steps of food processing. The Deposited Bacteriophages can additionally be introduced into packaging materials used to contain food product(s), prior to or following transfer of the food product(s) to the packaging materials. Alternatively the Deposited Bacteriophages can be useful in the local processing of food products located, for example, in the home or in a restaurant kitchen, using the same modes of contact as described supra.

In another embodiment of the invention, the Deposited Bacteriophages are added as a component of paper products, either during processing or after completion of processing of the paper products. Paper products to which the Deposited Bacteriophages may be added include, but are not limited to, paper towels, toilet paper, moist paper wipes. In a preferred embodiment of the invention, the Deposited Bacteriophages are added as a component of cleansing wipes. The Deposited Bacteriophages may be added in an aqueous state to a liquid-saturated paper product, or alternatively may be added in powder form, such as lyophilized, to dry paper products, or any combination thereof. In similar manner, the Deposited Bacteriophages may be incorporated into films such as those used for packaging foods, such as by impregnating or coating the film.

The methods of the invention further contemplate the application of the Deposited Bacteriophages to the floors, walls, ceilings, drains, or other environmental surfaces in structures such as the industrial food processing, military, or home environments. In a particularly preferred embodiment of the invention, the Deposited Bacteriophages are applied to refrigerated devices used to store or transport food or food products, including but not limited to, home and industrial refrigerators, deli-meat and cheese counters, refrigerated trucks, and mobile food-service vehicles.

In a non-limiting embodiment of the invention, the Deposited Bacteriophages of the invention are useful in preventing the colonization of, or inhibiting the growth of, Targeted Bacteria on processed or unprocessed food products by infecting, lysing or inactivating Targeted Bacteria present on said food product. Processed or unprocessed food products intended for humans in which the Deposited Bacteriophages are particularly useful in preventing the growth or colonization of Targeted Bacteria include, but are not limited to beef (particularly ground beef), food products made with ground beef such as hamburgers, sloppy joes, lasagna, stews, and other ground beef preparations, fresh vegetables exposed to Targeted Bacteria presumably via animal waste, such as lettuce, spinach, green onions, and other fresh vegetables commonly grown out of doors in fields, drinking water, and foodstuffs secondarily contaminated with Targeted Bacteria through contact with contaminated foods, sewage, or animal feces. Processed or unprocessed food products intended for animals in which the Deposited Bacteriophages are particularly useful include wet pet foods, moist pet foods, and dry pet foods intended for household pets, as well as feed intended for domesticated animals such as horses, cows, sheep, pigs, chickens, turkeys, and fish raised in farming or aquaculture environments.

The Deposited Bacteriophages can also be administered to potable and non-potable water sources to reduce or eliminate the presence of Targeted Bacteria.

Bacteriophage compositions of the invention may be provided in aqueous or non-aqueous embodiments for the preservation of food.

Aqueous embodiments of the Deposited Bacteriophages include aqueous compositions comprising, or alternatively consisting of, one of the Deposited Bacteriophages alone or in combination with other Deposited Bacteriophages, or with another bacteriophage or other bacteriophages. Aqueous embodiments of the Deposited Bacteriophages are available in solutions that include, but are not limited to, phosphate buffered saline, Luria-Bertani Broth or chlorine-free water.

Non-aqueous embodiments of the Deposited Bacteriophages include, but are not limited to, lyophilized compositions or spray-dried compositions comprising, or alternatively consisting of, the Deposited Bacteriophages alone or in combination with other bacteriophage(s). Freeze-dried and spray-dried compositions may also include soluble and/or insoluble carrier materials as, for example, processing aids.

The Deposited Bacteriophages can be administered at a concentration effective to prevent the initial colonization of foods with Targeted Bacteria, or to inhibit the growth or colonization of food or food products, as well as the equipment used to process or store food. In a non-limiting embodiment of the invention, the Deposited Bacteriophages typically administered at a growth inhibiting effective amount of a concentration of about $10^7$ to about $10^{11}$ Plaque Forming Units (PFU)/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.). The Deposited Bacteriophages at such concentrations may be applied at, for example, about 1 ml/500 cm$^2$ of food surface.

Food Processing Uses

The present invention provides a method for preventing growth of microorganisms on food products comprising contacting a food product with an effective amount of a composition comprising at least one of the Deposited Bacteriophage for the prevention of growth of *Listeria* microorganisms on food products. The prevention of growth of microorganisms on food products is intended to provide a food product that is devoid of or contains minimal numbers of viable microorganisms that could cause illness in humans or animals or spoilage of the food product prior to ingestion. The food product may be fruit juices, vegetable juices, produce, poultry, beef, lamb, or pork.

The prevention of growth of microorganisms on food products is intended to include but is not limited to the following mechanisms: (1) removal of attached microorganisms from the food products; (2) inhibition of attachment of microorganisms to the food products; (3) killing or inactivation of attached microorganisms on the food products; and (4) killing or inactivation of microorganisms which are not attached to the food product but which are present in liquids associated with the food products during processing; such as in chill tanks, or which are present on surfaces associated with food preparation, liquids remaining on such surfaces, such as countertops, cutting boards and sinks, and equipment used in food preparation and sanitization of the food.

The present invention has an important application in the food processing industry, as well as for home and institutional food preparation. The Deposited Bacteriophage compositions of the invention are readily available and the cost of carrying out the method of the present invention is not expensive as compared to existing antimicrobial processes. Unlike existing treatments using, for example, trisodium phosphate, the use of the Deposited Bacteriophage compositions of the invention does not alter the appearance, color, taste, or texture of the food product. Moreover, the Deposited Bacteriophage compositions of the invention are non-toxic.

The Deposited Bacteriophage composition is applied for a period of time sufficient to kill *Listeria* bacteria present on the food product. It is important that the application time of the Deposited Bacteriophage compositions is for a sufficient time to result in significant prevention of growth of *Listeria* on the food product.

The present invention also includes methods of contacting the Deposited Bacteriophage compositions of the invention with food products, including but not limited to, spraying or misting the compound on the food product, or by immersing the food product in a composition comprising at least one of the Deposited Bacteriophages of the invention.

The present invention is intended to encompass any method that contacts the Deposited Bacteriophage compositions of the invention with a food product by any direct means, including spraying, misting, dipping, or soaking. But the present invention also is intended to include contact of the Deposited Bacteriophage compositions of the invention with the food by indirect means, such as applying the Deposited Bacteriophage compositions of the invention to equipment or food product processing or preparation surfaces in which the food product is contacted during processing, preparation, storage, and/or packaging.

Any type of method of contact of the Deposited Bacteriophage compositions with the food product is are preferred as long if it is capable of allowing a short application time: A method that utilizes a cabinet that provides spraying or misting of the food product is useful in the present invention. Machinery for use in such cabinets on a processing line in a food processing plant are adaptable for reducing the application time to a minimum while still obtaining efficacious antimicrobial effects on the food.

The present method is useful, for example, in a poultry processing plant for treating post-chilled chickens that have been immersed in a chill bath of cold water. The chickens are removed from the chill bath and treated with the Deposited Bacteriophage compositions of the invention for an application time sufficient to result in significant prevention of growth of microorganisms on the chickens. The treated chickens are subsequently packaged without further washing or rinsing. However, the method optionally may include, if deemed necessary, at least one washing step of the chickens prior to packaging. The optional washing step may include spraying or misting the food product with water or immersing the food product in a container or tank of water.

Further, the method of the present invention can optionally include a determination step prior to contacting the food product with the Deposited Bacteriophage compositions of the invention to determine the presence of microorganisms on the food before treatment Any conventional methods for rapidly determining the presence of microorganisms can be utilized as the determination step, which for example, includes PCR and immunoassays.

Additionally, the method of the present invention optionally includes a step to determine the presence of the bacteriophage compositions of the invention on the surface of the food product after contact with the Deposited Bacteriophage compositions. This determination is performed immediately after the contacting step or after several washing steps. For example, the Deposited Bacteriophage compositions of the invention is extracted from the tissues of the food in a form suitable for high performance liquid chromatography (HPLC) analysis.

The food processing industry, as well as home, restaurant or institutional food preparation, is in need of more effective products and processes for the prevention of growth of a broad range of contaminating microorganisms on many different food products and/or surfaces that the food products and juices or liquids from the food come in contact. This is especially true for microorganisms which are attached to the surfaces of food. As a result of increasing numbers of illnesses caused by foodborne pathogenic microorganisms, the food processing industry now requires more effective processes for the removal and prevention of a broader spectrum of microorganisms, and particularly for pathogenic microorganisms, such as, *Listeria*, which are known to cause serious human diseases as a result of food contamination. The present invention provides a composition comprising at least one Deposited Bacteriophages of the invention and methods of preventing the growth of microorganisms on and in the food, as well as in liquids and on surfaces associated with food products and their preparation. This method of prevention is an important goal in preventing cross-contamination from infected food products; in removing attached microorganisms from food products; in inhibiting the attachment of microorganisms to the food products; and in preventing the growth of microorganisms that remain attached to the food products. Further, the method of the present invention can easily be adapted for use in a food processing plant.

Environmental Control

In another embodiment of the invention, the Deposited Bacteriophages are administered to environments to control the growth or viability of Targeted Bacteria. Environments in which the Deposited Bacteriophages are useful to control the growth or viability of Targeted Bacteria include, but are not limited to, abattoirs, meat processing facilities, feedlots, vegetable processing facilities, medical facilities (including hospitals, out-patient clinics, school and/or university infirmaries, and doctors offices), military facilities, veterinary offices, animal husbandry facilities, public and private restrooms, and nursing and nursing home facilities. The invention further contemplates the use of the Deposited Bacteriophages for the battlefield decontamination of food stuffs, the environment, and personnel and equipment, both military and non-military.

The Deposited Bacteriophages are additionally useful alone or in combination with other bacteriophage(s) and/or other compounds, for preventing the formation of biofilms, or controlling the growth of biofilms, in various environments. Aqueous embodiments of the Deposited Bacteriophages are available in solutions that include, but are not limited to, phosphate buffered saline, Luria-Bertani Broth or chlorine-free water. In a particularly preferred embodiment, the Deposited Bacteriophages are used to control biofilm formation and growth in municipal water systems, industrial water systems, and personal water systems, as well as biofilms present in refrigerated environments.

The modes of administration include, but are not limited to, spraying, hosing, and any other reasonable means of dispersing aqueous or non-aqueous Bacteriophage compositions, in an amount sufficiently high to inhibit the growth or viability of Targeted Bacteria. In a non-limiting embodiment of the invention, the Deposited Bacteriophages are useful in preventing the growth or viability of Targeted Bacteria by infecting, lysing or inactivating Targeted Bacteria present in said environment. Administration of the Deposited Bacteriophages composition includes application to the floors, walls, counter-tops, ceilings, drains or any other environmental surface.

Bacteriophage compositions of the invention are available in aqueous or non-aqueous embodiments discussed earlier for Food Preservation applications.

In another embodiment of the invention, the Deposited Bacteriophages are added as a component of paper products, either during processing or after completion of processing of the paper products. Paper products to which the Deposited Bacteriophages may be added include, but are not limited to, paper towels, toilet paper, and moist paper wipes. In a preferred embodiment of the invention, the Deposited Bacteriophages are added as a component of cleansing wipes; it may be added in an aqueous state to a liquid-saturated paper product, or alternatively may be added in powder form such as a lyophilized preparation, to dry paper products, or any combination thereof.

The Deposited Bacteriophages can be administered at a concentration effective to inhibit the growth or viability of Targeted Bacteria in a particular environment. In a non-limiting embodiment of the invention, the Deposited Bacteriophages are administered at a concentration of about $10^7$ to $10^{11}$ PFU/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.)

Probiotic Uses

The Deposited Bacteriophages may be formulated into probiotic compositions. The probiotic compositions may be administered to a patient, wherein the Deposited Bacteriophages lyse the Targeted Bacteria. This lysis of the Targeted Bacteria may lead to a better microflora balance and confer a health benefit on the patient.

Prevention or Treatment of Infection or Colonization

In another embodiment, the invention contemplates a method for the prevention or treatment of illnesses caused by the Targeted Bacteria, comprising contacting a microbial growth inhibiting effective amount of a bacteriophage composition comprising the Deposited Bacteriophages with a site or sites of infection of a host mammal infected with Targeted Bacteria.

The infected mammalian host may be a human host or animal host. In particular, the host may be a bovine, poultry, or porcine host. Prevention of the infection by Targeted Bacteria, or treatment of infected persons or animals, is particularly preferred in immuno-compromised persons, pregnant females, and newborns and infants, who maybe at an elevated risk of infection by Targeted Bacteria. The modes of contact include, but are not limited to, spraying or misting the bacteriophage composition on the infected mammalian host, by injecting at a site or sites of infection a pharmaceutically acceptable composition containing a concentration of the Deposited Bacteriophages sufficiently high to inhibit the growth of Targeted Bacteria, or by ingesting a solution containing a concentration of the Deposited Bacteriophages sufficiently high to inhibit the growth of Targeted Bacteria. Additional routes of administration include but are not limited to oral, rectal, topical, ophthalmic, buccal, intravenous, otic, nasal, vaginal, inhalation, and intrapleural.

In another nonlimiting embodiment of the invention, the Deposited Bacteriophages are useful for preparing bacterial vaccines or bacterins that eliminate or reduce colonization of the Targeted Bacteria in, and/or their being shed by, various agriculturally-important animals. One example of a practical application for that type of vaccine is in the cattle-raising industry, where its administration may significantly reduce colonization of cattle with the Targeted Bacteria; thus, improving public safety by reducing contamination of beef with the Targeted Bacteria.

Bacteriophage compositions of the invention are available in aqueous or non-aqueous embodiments discussed earlier for Food Preservation applications.

The Deposited Bacteriophages can be administered at a concentration effective to inhibit the growth or viability of Targeted Bacteria in the infected host. In a non-limiting embodiment of the invention, the Deposited Bacteriophages are administered at a concentration of about $10^7$ to $10^{11}$ PFU/ml. One of skill in the art is capable of ascertaining bacteriophage concentrations using widely known bacteriophage assay techniques (Adams, M. H. (1959). Methods of study bacterial viruses. Bacteriophages. London, Interscience Publishers, Ltd.: 443-519.)

Depending on the severity of peculiarities of the infection, the Deposited Bacteriophages can be administered to animals (including humans) (i) orally, in tablet or liquid formulation ($10^5$-$10^{11}$ PFU/dose), (ii) rectally, (iii) locally (skin, eye, ear, nasal mucosa, etc.), in tampons, rinses and creams, (iv) as aerosols or intrapleunal injections and (v) intravenously.

Use of Bacteriophage Derivatives

Derivatives, such as polypeptides, including but not limited to bacteriophage lytic enzymes, encoded by the bacteriophage or the bacteriophage progeny are used for applications designed to prevent the growth of Targeted Bacteria through cell wall lysis. In this context, lytic polypeptides are useful for the prevention of the growth of Targeted Bacteria on processed and unprocessed food products, as well as equipment used for the processing of said food products.

In another preferred embodiment of the invention, bacteriophage derivatives are useful for the treatment of one or more infections in a mammal, including humans, by administering their therapeutically effective amounts to the patient. This method is useful for the treatment of infections of the gastrointestinal system. Similarly, this method is useful in a prophylactic setting for the prevention of infection by Targeted Bacteria in pregnant mammals, including humans. This method of treatment is further useful for the prevention or other disorders or infections caused by Targeted Bacteria, such as acute bloody or non-bloody diarrhea, sometimes associated with hemolytic-uremic syndrome.

Another nonlimiting embodiment of the invention is that the bacteriophage derivatives such as lysins will be useful for preparing bacterial vaccines or bacterins that eliminate or reduce colonization of the Targeted Bacteria in, and/or their being shed by, various agriculturally-important animals. One example of a practical application for that type of vaccine is in the cattle-raising industry, where administration of such vaccines/bacterins may significantly reduce colonization of cattle with the Targeted Bacteria; thus, improving public safety by reducing contamination of beef with the Targeted Bacteria.

Detection Systems

The Deposited bacteriophage, its progeny, recombinant bacteriophage, or derivatives of the above are useful in methods of screening environmental samples (including food products and food processing equipment) and clinical specimens for the presence of viable cells of Targeted Bacteria. For example, in one such system, recombinant bacteriophage containing a reporter system such as, for example, a luciferase reporter system is applied to the sample and analyzed at some time point in the future for the activation of the reporter molecule. The activation of the reporter molecule is indicative of the presence of viable cells of Targeted Bacteria.

The Deposited bacteriophage, their progeny, recombinant bacteriophage, or derivatives such as lytic enzymes are useful in methods of screening environmental samples including food products and food processing equipment and clinical specimens for the presence of viable cells of Targeted Bacteria, by monitoring and measuring bacterial metabolism products such as bacterial adenosine kinase (AK) or adenosine triphosphate (ATP) released as a result of specific lysis of Targeted Bacteria. For example, when the released ATP is incubated with a luciferin/luciferase mixture, a rapid flash of peak light emission occurs within less than a second, followed by a steady glow lasting for several hours. By measuring the luminescence, it is possible to obtain a quantitative estimate of the number of bacterial cells in a sample. Although the basic approach involved in such detection-based assays is fairly well-established, the existing assays have shortcomings that hinder their wide acceptance. For example, the various reagents that have been used to lyse bacteria and release their ATP have broad-specificity; therefore, ATP is released from all susceptible bacterial and eukaryotic cells present in the sample, which can cause false-positive readings. In this context, the original Deposited Bacteriophage, its progeny, recombinant bacteriophage, or derivatives such as lytic enzymes will specifically lyse Targeted Bacteria without affecting any other prokaryotic or eukaryotic cells that may be present in the sample, thus providing means for accurately and specifically identifying and detecting Targeted Bacteria.

Epidemiological Typing

The Deposited Bacteriophage, and/or their progeny and derivatives may be further useful as a tool for the epidemiological typing of Targeted Bacteria. For example, one of skill in the art can use the Deposited Bacteriophages of the invention to screen a panel of Targeted Bacteria isolates to aid in the taxonomic identification of the Targeted Bacteria, by determining which isolates yield a positive lytic reaction to the Deposited bacteriophage. For example, see (van der Mee-Marquet, N., M. Loessner, et al. (1997). "Evaluation of seven experimental phages for inclusion in the international phage set for the epidemiological typing of *Listeria monocytogenes*." Appl Environ Microbiol 63(9): 3374-3377.).

Preparation of Vaccines or Bacterins

The Deposited Bacteriophage, and/or its progeny and derivatives, also may be valuable for preparing bacterial lysates to be used as vaccines or bacterins. The immunogenicity of such vaccines or bacterins may be superior to that of so-called dead cell vaccines because phage-mediated lysis is a more effective and gentler approach for exposing protective antigens of bacteria than are approaches used to prepare the latter vaccines. For example, methods commonly used to inactivate bacterial pathogens for dead-cell vaccines, including but not limited to heat treatment, UV-irradiation, and chemical treatment, may deleteriously affect a vaccine's effectiveness by reducing the antigenicity of relevant immunological epitopes (Holt, et al. (1990). "Immunisation of pigs with killed cultures of *Streptococcus* suis type 2." Res Vet Sci 48(1): 23-27.; Melamed, et al. (1991). "A vaccine against avian colibacillosis based on ultrasonic inactivation of *Escherichia coli*." Avian Dis 35(1): 17-22.; Lauvau, et al. (2001). "Priming of memory but not effector CD8 T cells by a killed bacterial vaccine." Science 294(5547): 1735-1739). The presence of viable bacteriophage may also serve as an additional efficacy-enhancing factor, increasing the effectiveness of a phage lysate via their antibacterial effect on the Targeted Bacteria.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The invention may be practiced in ways other than those particularly described in the foregoing description and examples. The teachings provided herein of the invention can be applied to other purposes, other than the examples described below.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

EXAMPLES

The invention will be described below on the basis of special embodiments, which, however, are in no way to be taken to mean a restriction of the general inventive concept. These examples and methods are specific embodiments; however, the present invention is not limited to these examples and methods. It is known to the person skilled in the art that the invention can be carried out in the same manner by modifying the examples and methods described and/or by replacing individual examples or methods or parts of examples or methods by alternative examples or methods or alternative parts of examples or methods.

Example 1

Deposited Bacteriophages Isolation

LMSP-25, LMTA-34, LMTA-57, LMTA-94, and LMTA-148 were isolated from various water estuaries and reservoirs in Maryland (including Baltimore's Inner Harbor) using lysis of the Targeted Bacteria to form plaques in bacterial lawns as a means of detecting the presence of bacteriophage having lytic specificity for the Targeted Bacteria. Plaques were harvested, diluted, and re-plated on bacterial lawns through a process of serial enrichment until a single bacteriophage species, or monophage, was obtained as determined by a stable restriction fragment length profile of the bacteriophage DNA. The isolates obtained using the technique recited supra may be cultured using the techniques as set forth herein. The bacteriophage was deposited with the ATCC.

Example 2

Deposited Bacteriophages Concentration

Concentration of the Deposited Bacteriophages may be determined using techniques known in the art (Adams, M. H. (1959). Methods of study bacterial viruses. Bacteriophages. London, Interscience Publishers, Ltd.: 443-519.) When a single phage particle encounters a permissive bacterium it will lyse it with the concomitant release of newly formed phage particles. When phages are mixed with host cells and poured in a layer of soft agar on the surface of a nutrient agar plate supporting bacterial growth, the cells will resume growth. In areas where no phages are present the bacteria will grow to stationary phase, forming a smooth opaque layer or lawn in the overlay. In areas where phages are present, phage progeny from each infected bacterium will infect neighboring bacteria, resulting in a growing zone of lysis full of liberated phage which eventually becomes visible to the naked eye as a plaque in the otherwise smooth bacterial lawn. These plaques can be counted, and their number is widely used for expressing phage titer in plaque-forming units or PFU. Using this approach, concentration of the Deposited Bacteriophages may be determined. Briefly: (1) Various dilutions of the Deposited Bacteriophages preparation are prepared; for example, by mixing 0.1 ml of phage sample with 9.9 ml of sterile LB broth. The samples are gently but thoroughly mixed. 0.5 ml of this mixture (which is a $10^{-2}$ dilution of the original sample) is mixed with 4.5 ml of sterile LB broth ($10^{-3}$ dilution). Several 10-fold dilutions are prepared in a similar fashion; (2) the contents of the tubes (1 ml of various dilutions) are transferred into sterile 10 ml culture tubes and 0.1 ml of host bacterial culture are added. The sample is mixed gently before proceeding immediately to the next step; (3) 3-5 ml of warm (45-50° C.) 0.7% LB agar (top agar) are added. The sample is mixed quickly and very gently. Then, the entire contents of the culture tube are poured onto a plate containing solidified LB agar (bottom agar). The plates are slid in circles a few times on the bench top immediately after pouring; (4) after sitting at room temperature for 10 min to allow the top agar to harden, the plates are inverted and placed into a 37° C. incubator and incubated overnight; (5) the next morning, the number of plaques on the plate with 30-300 individual well-spaced plaques are counted and the titer calculated and expressed as PFU/ml of the starting sample.

Example 3

Production of the Deposited Bacteriophages

The Deposited Bacteriophages are produced using a culture system. More specifically, strain of the host Targeted Bacteria or other closely-related bacterial species on which the bacteriophage can propagate is cultured in batch culture, followed by inoculation of the bacteriophage at the pre-determined multiplicity of infection (MOI). Following incubation and bacterial lysis, the bacteriophage is harvested and purified and/or concentrated to yield phage progeny suitable for the uses enumerated herein. Purification and concentration procedures included variously processing through filtration system(s), centrifugation (including continuous-flow centrifugation) or other well known bacteriophage purification and concentration techniques (Adams, M. H. (1959). Methods of study bacterial viruses. Bacteriophages. London, Interscience Publishers, Ltd.: 443-519.)

The invention provides compositions comprising active viral particles of the bacteriophage capable of lysing strains of Targeted Bacteria. The concentration of bacteriophage is determined using phage titration protocols. The final concentration of the bacteriophage is adjusted by concentration, if a more concentrated phage composition is desired, via filtration, centrifugation, or other means, or by dilution, if a less concentrated phage composition is desired, with water or buffer to yield a phage titer of $10^6$ to $10^{12}$ PFU/ml, preferably $10^{10}$ to $10^{11}$ PFU/ml. The resulting bacteriophage compositions are generally stored at 4° C.; alternatively, preparations can be freeze or spray-dried for storage, or can be encapsulated and stabilized with protein, lipid, polysaccharide, or mixtures thereof. Upon reconstitution, the phage titer can be verified using phage titration protocols and host bacteria. One of skill in the art is capable of determining bacteriophage titers using widely known bacteriophage assay techniques (Adams, M. H. (1959). Methods of study bacterial viruses. Bacteriophages. London, Interscience Publishers, Ltd.: 443-519.)

Example 4

Application of the Deposited Bacteriophages for Preservation of Food Products

The bacteriophage produced using the methods of the present invention may be dispersed in an appropriate aqueous solution or lyophilized or freeze-dried powder and applied to the surface of food products. Alternatively, the bacteriophage may be included with a cheese culture or other microbially active foodstuff prior to or during processing.

Example 5

Isolation of the Bacteriophage DNA

Bacteriophage DNA, a derivative of the bacteriophage, can be used for various applications such as for preparing DNA-based vaccines, and also for analytical purposes, for identifying the bacteriophage such as RFLP profile determination and comparison. Phage DNA can be isolated using a suitable commercial kit such as the Lambda Mini Kit (Qiagen, Inc.; Valencia, Calif.) or the standard phenol extraction technique. For example, 0.75 ml of phage in phosphate-buffered saline solution at a titer of $10^8$-$10^{11}$ PFU/ml is collected. 10 µl of Proteinase K (20 mg/ml) and 2 µl of RNAse (10 mg/ml) is added, followed by incubation at 37° C. for 30 minutes, and a subsequent incubation at 56° C. for 30 minutes. Following incubation, 75 µl of a mixture of 10% SDS (0.1 ml), 0.5 M EDTA (0.1 ml) and 0.8 ml of water is added and incubated at room temperature for 5 min. 0.75 ml of a phenol:chloroform:isoamylalcohol (25:24:1) solution is mixed well with the sample, followed by centrifugation at 13,000 RPM for five (5) min. Next, the supernatant (approximately 600 µl) is carefully removed and transferred to a clean eppendorf tube. 0.6 ml of chloroform is added to the supernatant, mixed well, and centrifuged at 13,000 RPM for five (5) min. The supernatant is then carefully extracted (approximately 500 µl). Next, 0.1 volumes of 3M sodium acetate (40 ml) is added to the solution, followed by 2.5 volumes of cold 95% ethanol (1 ml) to precipitate the bacteriophage DNA. The solution is allowed to incubate at −20° C. for 1 hour, followed by centrifugation at 13,000 RPM for thirty (30) min. Following centrifugation, the pellet is washed with 1 ml of 70% cold ethanol, and the supernatant is poured from the pellet. The pellet is allowed to air dry, and is then resuspended in 30-300 µl of TE (10 mM tris-HCL, pH=8.0-8.5, 1 mM EDTA).

Example 6

Restriction Fragment Length Polymorphism (RFLP) Profile

RFLP can be used to identify the Deposited Bacteriophages or its progeny. The progeny will have a substantially equivalent RFLP DNA profile as the RFLP DNA profile of the original bacteriophage. A reference RFLP profile of the Deposited Bacteriophages are shown in FIG. 1. DNA was isolated from the bacteriophage using Qiagen Plasmid Miniprep or Midiprep kits (Valencia, Calif.) according to the manufacturer's directions. The DNA was quantitated by measuring absorbance at 260 nm. Approximately 0.5-1 µg of DNA was digested with an appropriate restriction enzyme (FIG. 1), and RFLP profile was determined on 1% agarose gel after staining with ethidium bromide.

Example 7

Lytic Specificity of the Deposited Bacteriophages

Nine hundred sixteen *Listeria* species strains were screened for their susceptibility to the Deposited Bacteriophages by the drop-on-lawn method, also known as the "spot test" method. Strains were streaked onto LB agar plates and incubated at 37° C. overnight. One colony of each strain was inoculated into a separate well of a 96-well microtiter plate containing LB broth and incubated at 37° C. until the OD600 reached 0.2-0.3. One hundred microliters of each strain were mixed with LB soft agar and poured onto an LB agar plate. After the soft agar hardened 10 µl of the bacteriophage were spotted in triplicate onto the plates inoculated with the strains of Targeted Bacteria. Lytic activity was observed after overnight incubation at 37° C. Lytic specificity results are presented in Table 1. One or more of the Deposited Bacteriophages lysed 721 (78.7%) of the 916 strains of Targeted Bacteria examined. In contrast, the Deposited Bacteriophages lysed 0 (0%) of 30 non-*Listeria* species strains (Table 2).

TABLE 1 shows the lytic specificity of the Deposited Bacteriophages for *Listeria* species, the Targeted Bacteria.

| *Listeria* Identity | LMSP-25 | LMTA-34 | LMTA-57 | LMTA-94 | LMTA-148 |
|---|---|---|---|---|---|
| Lm 1 | − | + | − | − | + |
| Lm 3 | − | − | − | − | + |
| Lm 4 | − | − | − | − | + |
| Lm 5 | − | − | − | − | − |
| Lm 6 | − | − | − | − | + |
| Lm 7 | − | − | − | − | + |
| Lm 8 | − | − | − | − | + |
| Lm 9 | − | − | − | − | + |
| Lm 10 | − | + | − | − | − |
| Lm 11 | + | + | + | − | − |
| Lm 12 | − | − | − | − | + |
| Lm 13 | − | − | − | − | + |
| Lm 14 | − | + | + | + | + |
| Lm 15 | − | − | − | − | − |
| Lm 17 | + | + | + | + | + |
| Lm 18 | + | + | + | + | + |
| Lm 19 | + | + | + | + | + |
| Lm 20 | − | − | − | − | − |
| Lm 21 | + | + | + | + | + |
| Lm 23 | + | + | + | + | + |
| Lm 24 | − | − | − | − | − |
| Lm 25 | + | + | + | + | − |
| Lm 26 | − | − | − | − | − |
| Lm 27 | − | − | − | − | − |
| Lm 28 | − | − | − | − | − |
| Lm 29 | + | + | + | + | + |
| Lm 30 | + | + | + | + | − |
| Lm 31 | − | − | − | − | − |
| Lm 32 | − | + | − | + | + |
| Lm 33 | + | + | + | + | + |
| Lm 34 | − | + | − | − | − |
| Lm 35 | − | − | − | − | − |
| Lm 36 | − | − | − | − | − |
| Lm 37 | − | − | − | − | − |
| Lm 38 | + | + | + | + | + |
| Lm 39 | − | − | − | − | − |
| Lm 41 | − | − | − | − | − |
| Lm 42 | − | − | − | − | − |
| Lm 43 | − | − | − | − | − |
| Lm 44 | − | + | − | + | + |
| Lm 45 | − | − | − | − | − |
| Lm 46 | − | − | − | − | − |
| Lm 47 | − | − | − | − | − |

TABLE 1-continued shows the lytic specificity of the Deposited Bacteriophages for *Listeria* species, the Targeted Bacteria.

| Listeria Identity | LMSP-25 | LMTA-34 | LMTA-57 | LMTA-94 | LMTA-148 |
|---|---|---|---|---|---|
| Lm 48 | − | − | − | − | − |
| Lm 49 | − | − | − | − | − |
| Lm 50 | − | + | − | − | − |
| Lm 51 | − | − | − | − | − |
| Lm 52 | − | − | − | − | − |
| Lm 53 | − | − | − | − | − |
| Lm 54 | − | − | − | − | − |
| Lm 55 | + | + | + | + | + |
| Lm 56 | − | − | − | − | + |
| Lm 57 | + | + | + | − | − |
| Lm 59 | + | + | + | + | + |
| Lm 61 | − | + | − | − | − |
| Lm 62 | − | − | − | − | − |
| Lm 63 | − | − | − | − | − |
| Lm 64 | + | + | + | + | − |
| Lm 65 | − | − | − | − | − |
| Lm 66 | − | − | − | − | − |
| Lm 67 | + | + | + | + | − |
| Lm 68 | + | + | + | + | + |
| Lm 69 | − | − | − | − | + |
| Lm 70 | + | + | + | + | + |
| Lm 71 | − | − | − | − | − |
| Lm 72 | + | + | + | + | + |
| Lm 73 | + | + | + | + | + |
| Lm 74 | + | + | + | + | + |
| Lm 75 | − | − | − | − | + |
| Lm 76 | − | − | − | − | − |
| Lm 77 | − | − | − | − | − |
| Lm 78 | + | + | + | + | + |
| Lm 79 | + | + | + | + | + |
| Lm 80 | + | + | + | + | + |
| Lm 81 | − | − | − | − | − |
| Lm 82 | + | + | + | + | + |
| Lm 83 | − | + | + | − | + |
| Lm 84 | + | + | + | − | + |
| Lm 85 | + | + | + | − | + |
| Lm 86 | + | + | + | + | + |
| Lm 87 | + | + | + | + | + |
| Lm 88 | + | + | + | + | + |
| Lm 89 | − | + | − | − | − |
| Lm 90 | + | + | + | + | + |
| Lm 91 | + | + | − | − | − |
| Lm 92 | − | − | − | − | − |
| Lm 93 | − | − | − | − | − |
| Lm 94 | + | + | + | + | + |
| Lm 95 | − | − | − | − | − |
| Lm 96 | − | − | − | − | − |
| Lm 97 | − | − | − | − | + |
| Lm 98 | − | − | − | − | − |
| Lm 99 | − | + | + | + | + |
| Lm 100 | + | + | + | + | + |
| Lm 101 | + | + | + | + | + |
| Lm 102 | + | + | + | + | + |
| Lm 103 | − | − | − | − | − |
| Lm 104 | − | + | + | − | + |
| Lm 105 | − | + | + | + | + |
| Lm 106 | − | − | − | − | + |
| Lm 107 | + | + | + | − | + |
| Lm 108 | + | + | + | + | + |
| Lm 109 | + | + | + | + | + |
| Lm 110 | − | − | − | − | − |
| Lm 111 | − | − | − | − | + |
| Lm 112 | − | − | − | − | + |
| Lm 113 | − | − | − | − | − |
| Lm 114 | + | + | + | + | + |
| Lm 115 | + | + | + | + | + |
| Lm 116 | − | − | − | − | − |
| Lm 117 | + | + | + | + | + |
| Lm 118 | + | + | + | + | + |
| Lm 119 | − | − | − | − | − |
| Lm 120 | + | + | + | + | + |
| Lm 121 | − | − | + | − | + |
| Lm 122 | − | − | − | − | − |
| Lm 123 | − | − | − | − | + |
| Lm 124 | − | + | − | − | − |
| Lm 125 | + | + | + | + | + |
| Lm 126 | + | + | + | + | + |
| Lm 127 | + | + | + | + | + |
| Lm 128 | + | + | + | + | + |
| Lm 129 | − | − | − | − | − |
| Lm 131 | − | − | − | − | − |
| Lm 132 | − | + | + | + | + |
| Lm 133 | − | − | − | − | − |
| Lm 134 | − | − | − | − | − |
| Lm 135 | − | − | − | − | + |
| Lm 136 | − | − | − | + | − |
| Lm 137 | − | − | − | − | − |
| Lm 138 | − | − | − | − | − |
| Lm 139 | − | − | − | + | − |
| Lm 140 | − | + | + | + | + |
| Lm 142 | + | + | + | + | + |
| Lm 143 | − | − | − | + | + |
| Lm 144 | − | + | − | + | + |
| Lm 145 | − | − | − | − | + |
| Lm 146 | + | + | + | + | + |
| Lm 147 | + | + | + | + | + |
| Lm 148 | + | + | + | + | + |
| Lm 149 | + | + | + | + | + |
| Lm 150 | − | − | − | − | − |
| Lm 151 | − | − | − | − | − |
| Lm 152 | − | + | + | + | + |
| Lm 153 | − | − | − | − | − |
| Lm 155 | + | + | + | + | + |
| Lm 157 | + | + | + | + | + |
| Lm 159 | + | + | + | + | + |
| Lm 164 | − | − | − | − | + |
| Lm 165 | − | − | − | − | − |
| Lm 166 | − | − | − | − | + |
| Lm 169 | + | + | + | − | + |
| Lm 170 | + | + | + | + | − |
| Lm 171 | + | + | + | + | + |
| Lm 172 | + | + | + | + | + |
| Lm 173 | + | + | + | + | + |
| Lm 174 | − | − | − | − | − |
| Lm 175 | + | + | + | + | + |
| Lm 176 | + | + | + | + | − |
| Lm 177 | + | + | + | + | + |
| Lm 178 | + | + | + | + | + |
| Lm 183 | − | − | − | − | − |
| Lm 184 | − | − | − | − | − |
| Lm 185 | − | + | − | − | − |
| Lm 191 | − | − | − | − | − |
| Lm 192 | − | − | − | − | − |
| Lm 193 | − | − | − | − | − |
| Lm 194 | − | − | − | − | − |
| Lm 195 | − | − | − | − | + |
| Lm 196 | − | − | − | − | − |
| Lm 198 | − | − | − | − | − |
| Lm 200 | + | − | + | + | + |
| Lm 201 | − | − | − | − | − |
| Lm 229 | − | − | − | − | − |
| Lm 230 | − | − | − | − | − |
| Lm 249 | − | − | − | − | − |
| Lm 250 | − | − | − | − | − |
| Lm 251 | − | − | − | − | − |
| Lm 252 | − | − | − | − | − |
| Lm253-35152 | + | − | + | + | + |
| Lm254-13932 | + | + | − | − | − |
| Lm 255 | + | + | + | + | + |
| Lm 256 | + | − | + | + | + |
| Lm 257 | + | + | + | + | + |
| Lm 258 | + | + | + | + | + |
| Lm 259 | + | + | + | + | + |
| Lm 260 | − | + | − | − | − |
| Lm 261 | + | + | + | + | + |
| Lm 262 | + | + | + | + | + |

TABLE 1-continued shows the lytic specificity of the Deposited Bacteriophages for *Listeria* species, the Targeted Bacteria.

| Listeria Identity | LMSP-25 | LMTA-34 | LMTA-57 | LMTA-94 | LMTA-148 |
|---|---|---|---|---|---|
| Lm 263 | + | + | + | + | + |
| Lm 300 | − | − | − | − | − |
| Lm 301 | + | + | + | + | + |
| Lm 302 | − | − | − | − | − |
| Lm 303 | − | − | − | − | − |
| Lm 304 | + | + | + | + | + |
| Lm 305 | − | − | − | − | − |
| Lm 306 | − | − | − | − | − |
| Lm 307 | − | − | − | − | − |
| Lm 308 | − | − | − | − | − |
| Lm 309 | − | − | − | − | − |
| Lm 310 | − | − | − | − | − |
| Lm 311 | − | − | − | − | − |
| Lm 312 | − | − | − | − | − |
| Lm 313 | − | − | − | − | − |
| Lm19117 | + | + | + | + | + |
| Lm19118 | − | − | − | − | − |
| Lin 51742 | + | + | + | + | + |
| Lm19116 | + | + | + | − | + |
| Lin33090 | − | − | − | − | − |
| Lm7644 | + | + | + | + | + |
| Lm19115 | + | + | + | + | + |
| Lm15313 | + | + | + | − | + |
| Lwe35897 | − | − | − | − | + |
| Lm19114 | − | − | − | − | − |
| Lm49594 | + | + | + | + | + |
| 148113 | − | − | − | − | − |
| 148117 | − | − | − | − | − |
| 148144 | − | − | − | − | − |
| 148145 | − | − | − | − | − |
| 148151 | − | − | − | − | − |
| 148128 | − | − | − | − | − |
| 148158 | − | − | − | − | − |
| 148164 | − | − | − | − | − |
| 151840 | − | − | − | − | − |
| 152433 | − | − | − | − | − |
| 155818 | − | − | − | − | − |
| Lm 51780 | + | + | + | + | + |
| Lm 144587 | − | − | − | − | − |
| Lm 150747 | − | − | − | − | − |
| Lm 150748 | − | − | − | − | − |
| L.wel150750 | − | + | − | + | − |
| L.m151839 | − | − | − | − | − |
| L.ino148155 | + | + | + | + | − |
| L.ino148163 | + | + | + | + | − |
| L.m 43249 | + | + | + | − | + |
| L.seeligeri 51334 | − | − | − | − | − |
| L.ivanovii 700402 | + | + | + | + | + |
| Lm ECL65 | + | + | + | + | + |
| Lm ECL64 | + | + | + | + | + |
| Lm ECL53 | − | + | − | − | − |
| Lm ECL54 | − | + | − | − | − |
| Lm ECL55 | − | + | − | − | − |
| Lm ECL52 | + | + | + | + | + |
| Lm ECL63 | + | + | + | + | + |
| Lm ECL205 | + | + | + | + | + |
| Lm ECL346 | − | − | − | − | − |
| Lm 256-030701L037 | + | + | + | − | − |
| Lm 257-030529L002 | + | + | + | + | − |
| Lm 258-030523L016 | − | − | − | − | − |
| Lm 259-030610K005 | + | + | + | + | + |
| Lm 260-030624L002 | − | + | + | − | − |
| Lm 261-030617L002 | − | − | − | − | − |
| Lm 262-030610K003 | − | − | − | − | − |
| Lm 263-030627M002 | + | + | + | + | + |
| Lm 264-030624L001 | − | + | + | − | − |
| Lm ATCC 19111 | + | + | + | − | + |
| Lm ATCC BAA 839 | + | + | + | + | + |

Note:
$10^4$ PFU/ml phage concentration was used for spot testing.

TABLE 2 shows the lytic specificity of the Deposited Bacteriophages for non-Targeted Bacteria of the other bacterial species.

| Bacteria | Identity | 1 LMSP-25 | 2 LMTA-34 | 3 LMTA-57 | 4 LMTA-94 | 5 LMTA-148 |
|---|---|---|---|---|---|---|
| *Enterococcus* | ATCC 11823 | − | − | − | − | − |
| *Enterococcus* | ATCC 19433 | − | − | − | − | − |
| *E. coli* | ATCC 700728 | − | − | − | − | − |
| *E. coli* | ATCC 35321 | − | − | − | − | − |
| *E. coli* | ATCC 35322 | − | − | − | − | − |
| *E. coli* | ATCC 35335 | − | − | − | − | − |
| *E. coli* | ATCC 35342 | − | − | − | − | − |
| *E. coli* | ATCC 35343 | − | − | − | − | − |
| *E. coli* | ATCC 35351 | − | − | − | − | − |
| *E. coli* | ATCC 35352 | − | − | − | − | − |
| *Shigella* | ATCC 9290 | − | − | − | − | − |
| *Pseumonas* | ATCC 15692 | − | − | − | − | − |
| *Pseumonas* | ATCC 51674 | − | − | − | − | − |
| *Pseumonas* | ATCC 43390 | − | − | − | − | − |
| *Pseumonas* | ATCC 39324 | − | − | − | − | − |
| *Salmonella* | ATCC 19585 | − | − | − | − | − |
| *Salmonella* | ATCC 13311 | − | − | − | − | − |
| *Salmonella* | ATCC 9184 | − | − | − | − | − |
| *Salmonella* | ATCC 6962 | − | − | − | − | − |

TABLE 2-continued shows the lytic specificity of the Deposited Bacteriophages
for non-Targeted Bacteria of the other bacterial species.

| Bacteria | Identity | 1<br>LMSP-25 | 2<br>LMTA-34 | 3<br>LMTA-57 | 4<br>LMTA-94 | 5<br>LMTA-148 |
|---|---|---|---|---|---|---|
| Salmonella | ATCC 13076 | – | – | – | – | – |
| Salmonella | ATCC 10719 | – | – | – | – | – |

Note:
$10^9$ PFU/ml phage concentration was used for spot testing.

Example 8

Detection of Targeted Bacteria in Food Samples

The bacteriophage or its derivative, such as lytic enzyme, produced using the methods of the present invention is used to specifically lyse Targeted Bacteria without affecting any other prokaryotic or eukaryotic cells that may be present in the sample; thus, specifically eliciting their release of measurable bacterial products such as AK or ATP. Briefly: (1) Samples of the food to be analyzed are obtained and suspended in appropriate buffer, (2) The Deposited Bacteriophages are added to the suspensions, as a result of which the Targeted Bacteria cells present in the samples are lysed and their ATP is released, (3) A luciferin+luciferase preparation is added to the mixtures, and (5) The mixtures' luminescence is measured within 60 sec, and the results are displayed on a handheld luminometer. It may be possible to establish a correlation between the luminometer readings and the number of Targeted Bacteria cells lysed (in general, the average amount of ATP per bacterial cell is 0.5-1.0 fg; precise correlation between the luminometer readings and the number of Targeted Bacteria cells should be experimentally established). If Targeted Bacteria cells are not present in the food samples analyzed, bacterial lysis and ATP-release will not occur.

Example 9

Preparing Vaccines and Bacterins

One example of utilizing bacteriophages to prepare vaccines and bacterins is to use the lytic Deposited Bacteriophages to lyse specific strains of the Targeted Bacteria, which will yield bacterial lysates containing minimally-affected immunological epitopes of the bacteria. The phage may be removed from the final vaccine/bacterin preparation. Alternatively, it may be retained unaltered in the preparation because its lytic activity against Targeted Bacteria that may be present in the mammalian organism being vaccinated may increase the preparation's efficacy. In one preferred embodiment of the present invention: (i) the most prevalent, problematic strains of the Targeted Bacteria are chosen so that the vaccine/bacterin contains the immunological epitopes that are most relevant for protecting against the infection, and (ii) the bacteriophage is kept unaltered in the final vaccine/bacterin, at levels ranging from $10^6$-$10^{10}$ PFU/ml.

Bacteriophage-based vaccines and bacterins also may be prepared by using derivatives of the Deposited Bacteriophages to lyse the Targeted Bacteria. An example of the general methodology can be briefly outlined from a recent study (Panthel, K., W. Jechlinger, et al. (2003). "*Helicobacter pylori* ghosts by PhiX protein E-mediated inactivation and their evaluation as vaccine candidates." Infect Immun 71(1): 109-16.) of an *Helicobacter pylori* bacterin. The authors used *Listeria-H. pylori* shuttle plasmid pHel2 and lysis gene e of bacteriophage φX174 to construct *H. pylori* lysis plasmid pHPC38, which they introduced into *H. pylori* strain P79. At a pre-determined time, the authors triggered e gene-expression in order to elicit bacterial lysis, and they found that the lysate protected BALB/c mice against *H. pylori* infection.

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated bacteriophage LMSP-25 deposited under ATCC Accession No. PTA-8353, LMTA-34 deposited under ATCC Accession No. PTA-8354, LMTA-57 deposited under ATCC Accession No. PTA-8355, LMTA-94 deposited under ATCC Accession No. PTA-8356, or LMTA-148 deposited under ATCC Accession No. 8357, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

2. Isolated progeny of the bacteriophage of claim 1, which have RFLP DNA profiles substantially equivalent to the profile of said bacteriophage.

3. A composition comprising at least one of the isolated bacteriophages of claim 1.

4. A composition comprising at least one of the isolated bacteriophages of claim 2.

5. A food product comprising at least one of the isolated bacteriophages of claim 1.

6. A food product comprising at least one of the isolated bacteriophages of claim 2.

7. At least one derivative of the bacteriophage of claim 1, said derivative comprising nucleic acids, partial or complete genes, gene expression products, structural components, or one or more combinations thereof.

8. At least one derivative of the bacteriophage of claim 2, said derivative comprising nucleic acids, partial or complete genes, gene expression products, structural components, or one or more combinations thereof.

9. A method for the reduction in the incidence of food borne illnesses caused by *Listeria* strains comprising contacting a food product or products with a microbial growth inhibiting effective amount of a bacteriophage composition comprising at least one of the isolated bacteriophage LMSP-25 deposited under ATCC Accession No. PTA-8353, LMTA-34 deposited under ATCC Accession No. PTA-8354, LMTA-57 deposited under ATCC Accession No. PTA-8355, LMTA-94 deposited under ATCC Accession No. PTA-8356, or LMTA-148 deposited under ATCC Accession No. 8357, said bacteriophage having lytic activity against *Listeria* strains, and variants thereof, wherein said variants retain the phenotypic characteristics of said bacteriophage and wherein said bacteriophage and variants thereof have lytic activity against *Listeria* strains.

10. The method of claim 9, wherein said contact comprises spraying or misting the bacteriophage composition on the food product(s), by dipping or soaking the food product(s) in a solution containing a concentration of the bacteriophage composition sufficiently high to inhibit the growth of *Listeria* strains, or adding, injecting or inserting the bacteriophage composition into the food product(s).

* * * * *